(12) United States Patent
Stein et al.

(10) Patent No.: US 12,702,625 B2
(45) Date of Patent: Aug. 11, 2026

(54) SMART CONTAINERS, SENSORS, AND METHODS FOR MEDICATION MANAGEMENT

(71) Applicant: Digital Medical Technologies, LLC, New York, NY (US)

(72) Inventors: Joshua D. Stein, New York, NY (US); Michael C. Morena, New York, NY (US); Christopher Ryan Waldenburg, New York, NY (US); John D. Gusz, New York, NY (US); Ryan Liu, New York, NY (US); Mark Guirguis, New York, NY (US)

(73) Assignee: Digital Medical Technologies, LLC, New York, NY (US)

( * ) Notice: Subject to any disclaimer, the term of this patent is extended or adjusted under 35 U.S.C. 154(b) by 203 days.

(21) Appl. No.: 17/440,674

(22) PCT Filed: Mar. 20, 2020

(86) PCT No.: PCT/US2020/023789
§ 371 (c)(1),
(2) Date: Sep. 17, 2021

(87) PCT Pub. No.: WO2020/191267
PCT Pub. Date: Sep. 24, 2020

(65) Prior Publication Data

US 2022/0160585 A1 May 26, 2022

Related U.S. Application Data

(60) Provisional application No. 62/867,167, filed on Jun. 26, 2019, provisional application No. 62/821,001, filed on Mar. 20, 2019.

(51) Int. Cl.
*A61J 7/04* (2006.01)
*A61J 1/03* (2023.01)
(Continued)

(52) U.S. Cl.
CPC ............ *A61J 7/0436* (2015.05); *A61J 1/035* (2013.01); *A61J 7/0069* (2013.01); *A61J 7/0076* (2013.01);
(Continued)

(58) Field of Classification Search
CPC ....... G16H 20/13; A61J 1/035; A61J 2200/30; A61J 7/0069; A61J 7/0076; A61J 7/0418; A61J 7/0481; A61J 7/0436; A61J 2200/70
(Continued)

(56) References Cited

U.S. PATENT DOCUMENTS 7,928,835 B1 4/2011 Jovanov et al.
8,754,769 B2 6/2014 Stein et al.
(Continued)

FOREIGN PATENT DOCUMENTS

CA 3074924 A1 9/2021
CN 103300819 A 9/2013
(Continued)

OTHER PUBLICATIONS

Varadarajan, Ranjani; The Effect of Illumination on Medication Preparation Errors in a Long Term Care Facility; Auburn University. ProQuest Dissertations Publishing, 2011. 3480692 (Year: 2011).*
(Continued)

*Primary Examiner* — Hiep V Nguyen
(74) *Attorney, Agent, or Firm* — Mintz Levin Cohn Ferris Glovsky and Popeo, P.C.

(57) ABSTRACT

An apparatus for medication management. The apparatus includes a housing for a packet of medication, a sensor coupled to the housing for sensing whether the packet has been removed or is likely to have been removed from the housing, and a transmitter for wirelessly transmitting data regarding a reading of the sensor to a remote computer. A system for medication management communicates with the
(Continued)

apparatus for medication management is provided. The remote computer is configured to send an alert to an external device, and the alert is based on the reading of the sensor. Also, an apparatus for medication management includes a housing for medication, and a sensor for sensing a quantity of medication within the housing. The sensor includes a plurality of conductive electrodes arranged in an interleaved pattern, and provided in a substantially horizontal position. Related systems, methods, techniques and articles are also disclosed.

16 Claims, 18 Drawing Sheets

(51) Int. Cl.
*A61J 7/00* (2006.01)
*G16H 20/13* (2018.01)

(52) U.S. Cl.
CPC ........... *A61J 7/0418* (2015.05); *A61J 7/0481* (2013.01); *G16H 20/13* (2018.01); *A61J 2200/30* (2013.01); *A61J 2200/70* (2013.01)

(58) Field of Classification Search
USPC .............................................................. 705/2
See application file for complete search history.

(56) References Cited

U.S. PATENT DOCUMENTS

| | | | | |
|---|---|---|---|---|
| 9,125,798 | B2 | 9/2015 | Stein et al. | |
| 9,358,183 | B2 | 6/2016 | Stein et al. | |
| 10,071,023 | B2 | 9/2018 | Stein et al. | |
| 2012/0160716 | A1 | 6/2012 | Chan et al. | |
| 2013/0222135 | A1 | 8/2013 | Stein et al. | |
| 2014/0058561 | A1 | 2/2014 | Rothschild | |
| 2014/0058755 | A1 | 2/2014 | Macoviak et al. | |
| 2014/0262918 | A1 | 9/2014 | Chu | |
| 2016/0000657 | A1 * | 1/2016 | Dickie | A61J 7/0084 206/534 |
| 2016/0000857 | A1 | 1/2016 | Bachovchin et al. | |
| 2016/0212389 | A1 * | 7/2016 | Mehrotra | A61J 7/04 |
| 2016/0354283 | A1 | 12/2016 | Cho et al. | |
| 2016/0357924 | A1 | 12/2016 | Jenkins | |
| 2016/0367435 | A1 | 12/2016 | Ahmadi | |
| 2017/0076060 | A1 | 3/2017 | Pilkington et al. | |
| 2017/0294105 | A1 | 10/2017 | Mehregany et al. | |
| 2018/0271437 | A1 | 9/2018 | Alhanbali | |
| 2018/0289591 | A1 | 10/2018 | French et al. | |
| 2018/0296441 | A1 | 10/2018 | Roham et al. | |
| 2020/0372986 | A1 * | 11/2020 | Shannon | G16H 50/70 |

FOREIGN PATENT DOCUMENTS

| | | | | |
|---|---|---|---|---|
| CN | 103415450 | A | 11/2013 | |
| CN | 105160199 | A | 12/2015 | |
| CN | 107145755 | A | 9/2017 | |
| JP | 2015516823 | A | 6/2015 | |
| JP | 2016-085481 | A | 5/2016 | |
| JP | 2018068743 | A | 5/2018 | |
| WO | WO-2003003970 | A1 | 1/2003 | |
| WO | WO-03075823 | A1 * | 9/2003 | A61J 7/0481 |
| WO | 2013126897 | A1 | 8/2013 | |
| WO | WO-2018064260 | A1 * | 4/2018 | A61J 7/0409 |
| WO | WO-2019011787 | A1 | 1/2019 | |
| WO | 2020191267 | A1 | 9/2020 | |

OTHER PUBLICATIONS

International Search Report and Written Opinion, mailed Aug. 3, 2020, International Patent Application No. PCT/US2020/023789, filed Mar. 20, 2020.

* cited by examiner 100
104
110a
110b
102

400
410a
404
410b
412
402

SMART CONTAINERS, SENSORS, AND METHODS FOR MEDICATION MANAGEMENT

RELATED APPLICATIONS

The present application claims priority to and is the 35 U.S.C. 371 United States National Phase application based on International Patent Application No. PCT/US2020/023789, filed on Mar. 20, 2020, and entitled "Smart Containers, Sensors, and Methods for Medication Management", which claims the benefit of and priority to the U.S. Provisional Patent Application No. 62/821,001, filed Mar. 20, 2019, entitled, "SMART MEDICATION CONTAINER FOR A BLISTER PACK", and U.S. Provisional Patent Application No. 62/867,167, filed Jun. 26, 2019, entitled, "SYSTEM AND METHOD FOR ANALYZING AND RESPONDING TO DATA", the disclosures of which are incorporated herein by reference in their entireties. The present disclosure relates to U.S. Pat. Nos. 7,928,835, 8,754,769, 9,125,798, 9,358,183, and 10,071,023, and PCT Publication No. WO 2018/064260 A1, the disclosures of which are incorporated herein by reference in their entireties.

FIELD OF THE DISCLOSURE

Provided are medication containers with sensors configured to sense removal of one or more doses of medication from a medical container or a blister pack within the medical container. Additionally, related systems and computer-implemented methods for determining and providing interventions to patients, caregivers, and/or other parties (e.g., pharmacies) are provided, for example, to improve or maintain a patient's adherence rate to a medication regimen.

BACKGROUND

According to estimates, more than 100 million people suffer from at least one chronic illness in the United States alone. Further, chronic illnesses lead to approximately seven out of every ten deaths in the United States each year. Medications are often prescribed to alleviate and treat the chronic illnesses, yet go unconsumed. With current levels of adherence to medication regimens at or below 50%, patients are not properly treating their chronic diseases, even though many have access to preventative or palliative medications. One reason for patients not taking their medication is forgetfulness by the patient. Other reasons include unclear or confusing instructions for medication or a prescription thereof, a lack of monitoring by a health care provider or pharmacy of a patient's adherence to a medication regiment, and disassociation among, and lack of communication with, the patient, healthcare provider, and/or the pharmacy.

Timely refills are of great importance to ensure sustained therapeutic effect. However, waiting on patients to report that a medication is short on supply is not a reliable solution.

Additionally, medications (e.g., medicines, meds, drugs, pills, pharmaceuticals and the like) are packaged in several different types of containers. Conventional medication containers, however, do not safely secure the medication and do not provide easy access of the medication stored therein. Moreover, traditional medication containers do not detect whether or when the medication has been removed from the medication container, much less do so accurately. Conventional medication containers further do not have communication capabilities that enable communication with a remote server computer that may use the communicated data to generate reminders and alerts for a patient, or enable improved management of the refill process by, for example, triggering a reminder that fewer than a threshold number of doses remain in the medication container. Furthermore, traditional medication containers are wasted after every use.

Systems and methods have been provided for improving patient adherence to medication regimens, which, in turn, improve patient outcomes and quality of life. For instance, some of the systems and methods, are configured with sensors for determining whether and/or when a patient is taking the patient's medication and, when appropriate, providing reminders and/or alerts to the patient to improve adherence to a medication regimen.

Improved systems and methods are desired to effectively reduce forgetfulness by the patient, improve clarity of instructions for medication or the prescription thereof, promote monitoring by a health care provider or pharmacy of the patient's adherence to a medication regiment, improve association among and communication with the patient, healthcare provider, and/or the pharmacy, and for specific configuration and use with blister packs.

SUMMARY

The innovations described in the claims each have several features, no single one of which is solely responsible for desirable attributes. Without limiting the scope of the claims, some prominent features of the present disclosure will now be briefly described.

The present disclosure provides an apparatus for medication management. The apparatus may include a housing for a packet of medication. The apparatus may include a sensor coupled to the housing for sensing whether the packet has been removed or is likely to have been removed from the housing. The apparatus may include a transmitter for wirelessly transmitting data regarding a reading of the sensor to a remote computer.

The packet may include a plurality of projections positioned on a backing and each projection houses a portion of medication. The projections may be arranged in a grid format of multiple rows and columns of projections.

The housing may include a first housing and a second housing. The sensor may include a first sensor coupled to the first housing. The sensor may include a second sensor coupled to the second housing. The first sensor may be proximate to the second sensor in a first state of the first housing and the second housing disposed in a closed position. The first sensor may be positioned a spaced distance apart from the second sensor in a second state of the first housing and the second housing disposed in an open position.

The first housing may be a base. The second housing may be a top. The top may be coupled via a hinge to the base along a long edge of each of the base and the top. The first sensor and the second sensor may be provided opposite the hinge.

The first housing may be a base. The second housing may be a cap. The cap may be coupled via a hinge to the base along a short edge of each of the base and the cap. The first sensor and the second sensor may be provided proximate to the short edge.

The first housing may be a base. The second housing may be a top. The top may be coupled via a hinge to the base along a short edge of each of the base and the cap. The first sensor and the second sensor may be provided opposite the short edge.

The first housing may be a base having an open end. The second housing may be a tray configured to slide into and out of the base via the open end of the base. The first sensor and the second sensor may be provided proximate to the short edge in the first state of the base and the tray disposed in a closed position.

The housing may include a base having an open end. The sensor may include a first sensor coupled to a first interior surface of the base. The sensor may include a second sensor coupled to a second interior surface of the base opposite the first interior surface. The first sensor and the second sensor may be positioned at or proximate to the open end.

The housing may include a base having a surface configured to be coupled to and decoupled from the packet. The sensor may include a first sensor coupled to the base. The sensor may include a second sensor coupled to the packet. The first sensor may be proximate to the second sensor in a first state of the base coupled to the packet. The first sensor may be positioned a spaced distance apart from the second sensor in a second state of the base decoupled from the packet.

The measurement sensor may include at least one from the group consisting of a magnet switch, a reed switch, a magnet sensor, a hall effect sensor, an optical sensor, a pressure sensor, a capacitance sensor, a capacitive touch sensor, an inductive touch sensor, a proximity sensor, and an electrical contact.

The present disclosure provides a system for medication management. The system may be configured to communicate with an apparatus for medication management. The apparatus may include a housing for a packet of medication. The apparatus may include a sensor coupled to the housing for sensing whether the packet has been removed or is likely to have been removed from the housing. The apparatus may include a transmitter for wirelessly transmitting data regarding a reading of the sensor to a remote computer. The remote computer may be configured to send an alert to one or more of the apparatus, a mobile communication device, and a computer. The alert may be based on the reading of the sensor.

The present disclosure provides a system for medication management, the system including a housing for medication. The housing may have an open end and a closed end opposite the open end. The system may include a sensor coupled to the housing for sensing a quantity of medication within the housing. The sensor may include a plurality of conductive electrodes arranged in an interleaved pattern for sensing the quantity of medication within the housing. The sensor may be provided proximate to the closed end. The sensor may be provided in the housing in a substantially horizontal position in a state of the housing in an upright position. The interleaved pattern of conductive electrodes may include regularly-spaced conductive electrodes. The interleaved pattern of conductive electrodes may include rectangularly shaped or generally rectangularly shaped conductive electrodes. A gap may be disposed between at least two of the plurality of conductive electrodes arranged in the interleaved pattern. A length of the gap may be about 1 mm.

The system may include one or more processors configured to trigger a reading of the sensor. The system may include a transmitter for wirelessly transmitting data regarding the reading of the sensor to a remote computer. The system may include a wireless receiver configured to receive an activation command from or otherwise initiated by the remote computer. The one or more processors may be configured to activate an alert based at least in part on the receipt of the activation command by the wireless receiver. At least one of the one or more processors may include one from the group consisting of a variable oscillating circuit, a resonant circuit, a Wein bridge oscillator, and a switched capacitor circuit.

The present disclosure provides a method for medication management. The method may include determining, with a processor, an orientation of a medication container based on a reading from a first sensor disposed on or in the medication container. The method may include collecting, with the processor, at least one first baseline reading from a second sensor disposed on or in the medication container based on the reading. The method may include collecting, with the processor, at least one second baseline reading from the second sensor after a delay time period. The method may include comparing, with the processor, the first baseline reading with the second baseline reading. The method may include sending, with the processor, an alert based on the comparison of the first baseline reading with the second baseline reading to an external device.

The present disclosure provides for a method for medication management. The method may include receiving, with a processor, patient messages related to a patient treated with the medication. The method may include receiving, with the processor, adherence device data from a container of the medication accessed by the patient. The method may include receiving, with the processor, health care information from at least one of a health care provider (HCP), an HCP computer, a pharmacist, and a pharmacy computer. The method may include processing, with the processor, at least one of the patient messages, the adherence device data, and the health care information with a model. The method may include outputting, with the processor, at least one of a patient's dosing history, a time a dose of the medication was administered with respect to a scheduled dose time, a signal in response to a determination that the dose was missed by the patient, a frequency and pattern of administered doses, and a frequency and pattern of missed doses. The method may include classifying, with the processor, the patient into one or more groups as to a likeliness to disenroll and a probability of disenrollment based on an output of the model.

The method may include processing, with the processor, the patient messages, the adherence device data, and the health care information with the model The method may include identifying, with the processor, a patient at risk of missing an additional dose based on the frequency and pattern of the missed doses. The method may include transmitting, with the processor, an intervention to the patient based on the identifying of the patient at risk.

The method may include classifying, with the processor, the patient messages with characteristics associated with a treatment plan for the patient. The method may include predicting, with the processor, an adherence probability based on the classified characteristics. The method may include transmitting, with the processor, an intervention to the patient or a patient support member or group based on the predicting of the adherence probability.

The method may include identifying, with the processor, a patient likely to miss a future dose or drop off the medication based on at least one of historical patient messages, the scheduled dose time, a number of the doses per day, and the adherence device data. The method may include transmitting, with the processor, an intervention to the patient or a patient support member or group based on the identifying of the patient.

For purposes of summarizing the disclosure, certain features, advantages and novel features of the innovations have been described herein. Not necessarily all advantages may be achieved in accordance with any particular exemplary embodiment. Thus, the innovations may be embodied or performed in a manner that achieves or optimizes one advantage or group of advantages as taught herein without necessarily achieving other advantages as may be taught or suggested herein.

BRIEF DESCRIPTION OF DRAWINGS

FIG. 1A illustrates a top view of a smart medication container configured to receive or couple to one or more blister packs containing medication according to a first exemplary embodiment of the present disclosure.

FIG. 1B illustrates a side view of the medication container of FIG. 1A.

FIG. 2A illustrates a top view of a smart medication container configured to receive or couple to one or more blister packs containing medication according to a second exemplary embodiment of the present disclosure.

FIG. 2B illustrates a side view of the medication container of FIG. 2A.

FIG. 3A illustrates a top view of a smart medication container configured to receive or couple to one or more blister packs containing medication according to a third exemplary embodiment of the present disclosure.

FIG. 3B illustrates an end view of the medication container of FIG. 3A.

FIG. 4A illustrates a top view of a smart medication container configured to receive or couple to one or more blister packs containing medication according to a fourth exemplary embodiment of the present disclosure.

FIG. 4B illustrates a side view of the medication container of FIG. 4A.

FIG. 5A illustrates a top view of a smart medication container configured to receive or couple to one or more blister packs containing medication according to a fifth exemplary embodiment of the present disclosure.

FIG. 5B illustrates a side view of the medication container of FIG. 5A.

FIG. 5C illustrates another side view of the medication container of FIGS. 5A and 5B.

FIG. 6A illustrates a side view of a smart medication container configured to receive or couple to one or more blister packs containing medication according to an exemplary embodiment of the present disclosure.

FIG. 6A illustrates another side view of a medication container according to an exemplary embodiment of the present disclosure.

Like reference symbols in the various drawings indicate like elements.

DETAILED DESCRIPTION

Systems and methods according to exemplary embodiments of the present disclosure enable and encourage improved medication adherence. Specifically, the present disclosure relates to apparatuses including a medication container configured to receive or couple to one or more blister packs containing medication, the medication container including one or more sensors configured to sense a condition indicative of removal of the one or more blister packs from the medication container and/or removal of one or more doses of medication from the one or more blister packs. The medication container may advantageously fulfill one or more (e.g., all) of the following objectives: safely secure the medication; permit easy access of the medication; detect that medication has been or is likely to have been removed from the one or more blister packs; and communicate, via a communication network, the details of detections by the medication container with a remote server computer that may use those details to generate reminders and alerts for a patient and/or other entity or facility, e.g., a pharmacy. The one or more blister packs may be removably inserted or coupled to the above-described medication container (e.g., by a patient or pharmacy representative). In some exemplary embodiments, the one or more sensors may activate or cause one or more actions by the medication container, e.g., storing and/or transmitting data indicative of whether medication has been or is likely to have been removed from the one or more blister packs, and/or cause one or more measurements (e.g., one or more measurements of a quantity of medication in the one or more blister packs).

As used herein, the term "blister pack" may include any suitable packet, including but not limited to a type of packet in which relatively small items are displayed and sold, a bubble packet, and the like. In some exemplary embodiments, the blister packet may include one or more projections (e.g., dome-shaped projections) positioned or mounted on a backing (e.g., a relatively firm backing). Each projection may be formed of plastic or similar material. The backing may be formed of a relatively thin foil, cardboard or similar material. In some exemplary embodiments, the backing of the packet may be rectangularly shaped or generally rectangularly shaped. In some exemplary embodiments, the packet may house medication in any suitable pattern, such as, for example, a grid wherein the medication is housed within projections of the packet arranged in a grid format, having multiple rows and columns of medication.

FIGS. 1A, 1B, 2A, 2B, 3A, 3B, 4A, 4B, 5A, 5B, 5C, 6A, and 6B illustrate smart medication containers according to exemplary embodiments of the present disclosure.

Figures 1A, 1B:
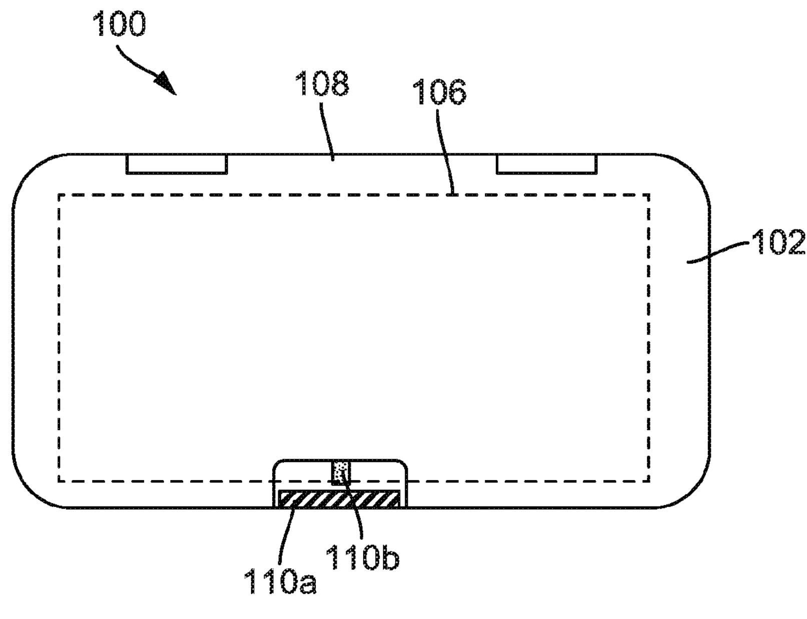
FIGS. 1A, 1B, 2A, 2B, 3A, 3B, 4A, 4B, 5A, 5B, 5C, 6A, and 6B illustrate smart medication containers configured to receive or couple to one or more blister packs containing medication according to exemplary embodiments of the present disclosure.

FIGS. 1A and 1B illustrate top and side views, respectively, of a first exemplary embodiment of a medication container 100. Medication container 100 includes base 102 and top 104 coupled to the base 102 (e.g., via a hinged connection) to permit top 104 to move from a first, closed position to a second, open position. Blister pack 106 may fit within medication container 100, and may be accessed by a user (e.g., patient) by moving top 104 from the first position to the second position. In some exemplary embodiments, top 104 may move relative to base 102 in a way that resembles opening of a clam shell. In some exemplary embodiments, each of base 102 and top 104 may have a rectangular or generally rectangular shape, although other shapes (e.g., square or generally square, circular or generally circular) are possible. In some exemplary embodiments, each of base 102 and top 104 may be elongate and generally flat. In some exemplary embodiments, top 104 may be coupled via a hinge to base 102 along a long edge 108 of each of base 102 and top 104.

In some exemplary embodiments, medication container 100 may include one or more sensors (110*a*, 110*b*). In some exemplary embodiments, the sensor may include a first sensor component 110*a* and a second sensor component 110*b*. The sensor may detect that top 104 is open and/or closed relative to base 102. In some exemplary embodiments, sensor component 110*a* may be disposed within or on top 104, and sensor component 110*b* may be disposed within or on base 102. Medication container 100 may detect that a blister pack has been removed or is likely to have been removed in a state when top 104 is open and/or closed (e.g., detecting that top 104 is opened, or detecting that top 104 is open (e.g., for some duration of time), and then closed).

In some exemplary embodiments, medication container 100 includes circuitry (e.g., one or more printed circuit boards and/or one or more printed circuit board assemblies) in communication with the one or more sensors (e.g., 110*a*, 110*b*). In some exemplary embodiments, medication container 100 includes a wireless circuit board that includes electronic components, e.g., a microprocessor, a wireless module, radio-frequency (RF) circuitry, and power circuitry. In some exemplary embodiments, the microprocessor may transmit, via a wireless antenna and to a server computer via a communication network. In some exemplary embodiments, the circuitry may be included in or on base 102. In other exemplary embodiments, the circuitry may be included in or on top 104. In still other exemplary embodiments, the circuitry may be included in or on both base 102 and top 104. Upon receipt of one or more outputs from the one or more sensors (e.g., one or more outputs indicating whether top 104 was opened and/or closed), the circuitry may store in a memory of the medication container 100 and/or transmit data (e.g., to a server) indicative of whether medication has been or is likely to have been removed from the one or more blister packs 106.

In some exemplary embodiments, the one or more sensors (e.g., 110*a*, 110*b*) may be positioned and configured to detect whether the one or more blister packs have been removed. For example, the one or more sensors may detect a blister pack, then detect an absence of the blister pack as the blister pack is removed, and/or then detect the blister pack once again as the blister pack is returned to medication container 100. In some exemplary embodiments, the one or more sensor components may be disposed in or on base 102 and/or top 104. In some exemplary embodiments, at least one sensor component may be included in or on blister pack 106. For example, a sensor component may be located into or on a blister pack 106 or other medication package. A sensor component on medication container 100 may determine that blister pack 106 has been removed and/or returned, obtain information regarding the medication, e.g., type of medication, batch of medication, and/or dosage, and/or obtain other information (e.g., a medication regimen for a particular patient for which blister pack 106 is intended).

In some exemplary embodiments, one or more outputs of the one or more sensors may be indicative of one or more measurements, for example, of a quantity of medication in the one or more blister packs 106.

Any suitable one or more sensors (e.g., 110*a*, 110*b*) may be utilized in connection with medication container 100. For example, the one or more sensors may include: one or more magnet and reed switches, one or more magnet and hall effect sensors, one or more optical sensors (e.g., infrared, visible light, or other), one or more pressure sensors (e.g., mechanical or solid state switch), one or more capacitance and/or capacitive touch sensors, one or more inductive touch sensors, one or more proximity sensors, and one or more electrical contacts.

Figure 2A:
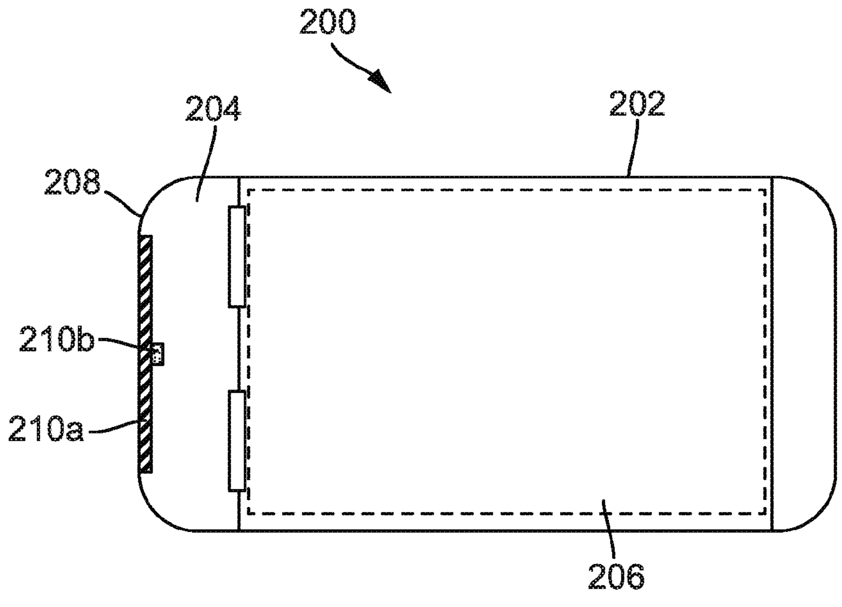
Figure 2B:
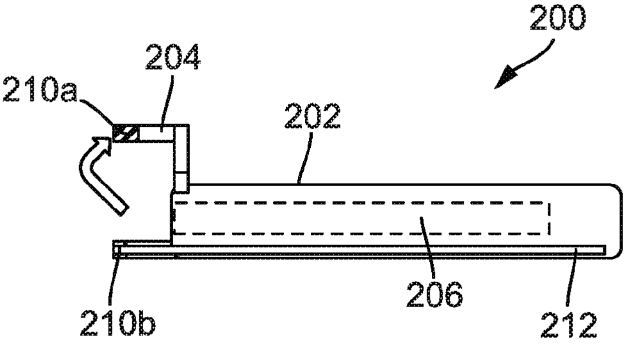

FIGS. 2A and 2B illustrate top and side views, respectively, of another exemplary embodiment of a medication container 200. Medication container 200 includes base 202 and cap or cover 204 coupled to the base (e.g., via a hinged connection) to permit cap 204 to move from a first, closed position to a second, open position. Blister pack 206 may fit within medication container 200, and may be accessed by a user (e.g., patient) by moving cap 204 from the first position to the second position. In some exemplary embodiments, base 202 may have a rectangular or generally rectangular shape, although other shapes (e.g., square or generally square, circular or generally circular) are possible. In some exemplary embodiments, base 202 may be elongate and generally flat. In some exemplary embodiments, cap 204 may be coupled via a hinge to base 202 along a short edge 208 of each of base 202 and cap 204. In some exemplary embodiments, blister pack 206 may be able to be slid in and out by a user through short edge 208 in a state when cap 204 is in an open position.

In some exemplary embodiments, medication container 200 may include one or more sensors (210*a*, 210*b*). In some exemplary embodiments, the sensor may include a first sensor component 210*a* and a second sensor component 210*b*. The sensor may detect that cap 204 is open and/or closed relative to base 202. In some exemplary embodiments, sensor component 210*a* may be disposed within or on cap 204, and sensor component 210*b* may be disposed within or on base 202. Medication container 200 may detect that a blister pack has been removed or is likely to have been removed in a state when cap 204 is open and/or closed (e.g., detecting that cap 204 is opened, or detecting that cap 204 is open (e.g., for some duration of time), and then closed).

In some exemplary embodiments, medication container 200 includes circuitry (e.g., one or more printed circuit boards and/or one or more printed circuit board assemblies 212) in communication with the one or more sensors (e.g., 210*a*, 210*b*). In some exemplary embodiments, medication container 200 includes a wireless circuit board that includes electronic components, e.g., a microprocessor, a wireless module, radio-frequency (RF) circuitry, and power circuitry. In some exemplary embodiments, the microprocessor may transmit, via a wireless antenna and to a server computer via a communication network. In some exemplary embodiments, the circuitry may be included in or on base 202. In other exemplary embodiments, the circuitry may be included in or on cap 204. In still other exemplary embodiments, the circuitry may be included in or on both base 202 and cap 204. Upon receipt of one or more outputs from the one or more sensors (e.g., one or more outputs indicating whether cap 204 was opened and/or closed), the circuitry may store in memory of medication container 200 and/or transmit data (e.g., to a server) indicative of whether medication has been or is likely to have been removed from the one or more blister packs.

In some exemplary embodiments, the one or more sensors (e.g., 210*a*, 210*b*) may be positioned and configured to detect whether the one or more blister packs have been removed. For example, the one or more sensors may detect a blister pack, then detect an absence of the blister pack as the blister pack is removed, and/or then detect the blister pack once again as the blister pack is returned to medication container 200. In some exemplary embodiments, the one or more sensor components may be disposed in or on base 202 and/or cap 204. In some exemplary embodiments, at least one sensor component may be included in or on blister pack 206. For example, a sensor component may be located into or on a blister pack 206 or other medication package. A sensor component on medication container 200 may determine that blister pack 206 has been removed and/or returned, obtain information regarding the medication, e.g., type of medication, batch of medication, or dosage, and/or obtain other information (e.g., a medication regimen for a particular patient for which blister pack 206 is intended).

In some exemplary embodiments, one or more outputs of the one or more sensors may be indicative of one or more measurements, for example, of a quantity of medication in one or more blister packs 206.

Any suitable one or more sensors (e.g., 210*a*, 210*b*) may be utilized in connection with medication container 200. For example, the one or more sensors may include: one or more magnet and reed switches, one or more magnet and hall effect sensors, one or more optical sensors (e.g., infrared, visible light, or other), one or more pressure sensors (e.g., mechanical or solid state switch), one or more capacitance and/or capacitive touch sensors, one or more inductive touch sensors, one or more proximity sensors, and one or more electrical contacts.

Figure 3A:
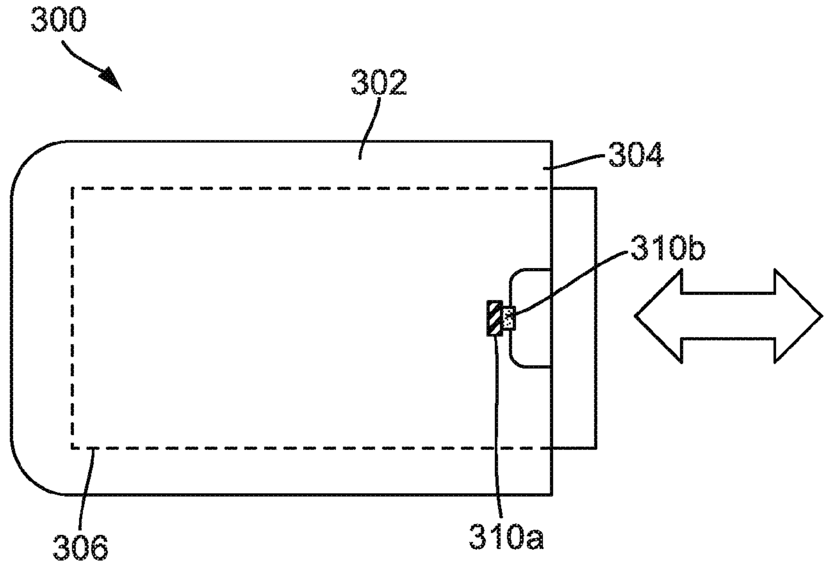
Figure 3B:
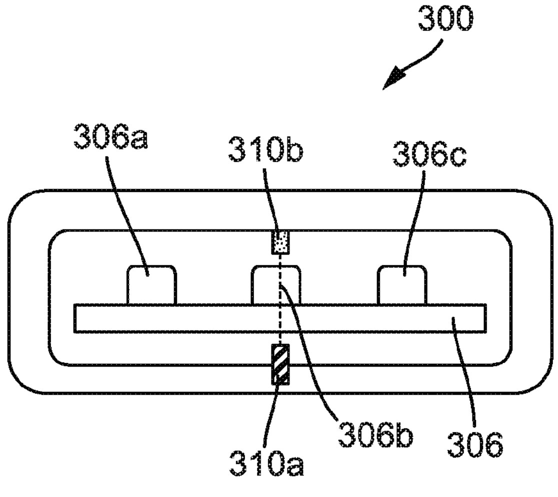

FIGS. 3A and 3B illustrate top and end views, respectively, of another exemplary embodiment of a medication container 300. Medication container 300 includes base 302 having an open end 304 (e.g., short end 304). Blister pack 306 may fit within medication container 300, and may be accessed by a user (e.g., patient) by sliding blister pack 306 in and out of open end 304 of base 302. In some exemplary embodiments, blister pack 306 may fit rigidly within base 302, for example, through a friction fit (e.g., one or more medication doses 306*a*, 306*b*, and 306*c* pressing against an interior surface of base 302 in a state when blister pack 306 is inserted within base 302). In some exemplary embodiments, base 302 may have a rectangular or generally rectangular shape, although other shapes (e.g., square or generally square, circular or generally circular) are possible. In some exemplary embodiments, base 302 may be elongate and generally flat. In some exemplary embodiments, in a state when blister pack 306 is fully inserted within base 302 at least a portion of blister pack 306 may extend past open end 304 (e.g., to permit a user to easily grip and remove blister pack 306).

In some exemplary embodiments, medication container 300 may include one or more sensors (310*a*, 310*b*). In some exemplary embodiments, a sensor may include a first sensor component 310*a* and a second sensor component 310*b*. The sensor(s) may detect that blister pack 306 is inserted within and/or removed from base 302. In some exemplary embodiments, sensor components 310*a* and 310*b* may be disposed within or on base 302 (e.g., one on or in a top surface of base 302 and the other on or in a bottom surface of base 302).

In some exemplary embodiments, medication container 300 includes circuitry (e.g., one or more printed circuit boards and/or one or more printed circuit board assemblies) in communication with the one or more sensors (e.g., 310*a*, 310*b*). The circuitry may be disposed, for example, on or in a bottom and/or top surface of base 302. In some exemplary embodiments, medication container 300 includes a wireless circuit board that includes electronic components, e.g., a microprocessor, a wireless module, radio-frequency (RF) circuitry, and power circuitry. In some exemplary embodiments, the microprocessor may transmit, via a wireless antenna and to a server computer via a communication network. Upon receipt of one or more outputs from the one or more sensors (e.g., one or more outputs indicating whether blister pack 306 was inserted and/or removed), the circuitry may store in memory of medication container 300 and/or transmit data indicative of whether medication has been or is likely to have been removed from the one or more blister packs.

In some exemplary embodiments, the one or more sensors (e.g., 310*a*, 310*b*) may be positioned and configured (e.g., at or proximate to open end 304) to detect whether the one or more blister packs have been removed. For example, the one or more sensors may detect a blister pack, then detect an absence of the blister pack as the blister pack is removed, and/or then detect the blister pack once again as the blister pack is returned to medication container 300. In some exemplary embodiments, at least one sensor component may be included in or on blister pack 306. For example, a sensor component may be located into or on a blister pack 306 or other medication package. A sensor component on medication container 300 may determine that blister pack 306 has been removed and/or returned, obtain information regarding the medication, e.g., type of medication, batch of medication, or dosage, and/or obtain other information (e.g., a medication regimen for a particular patient for which blister pack 306 is intended).

In some exemplary embodiments, one or more outputs of the one or more sensors may be indicative of one or more measurements, for example, of a quantity of medication in one or more blister packs 306.

Any suitable one or more sensors (e.g., 310*a*, 310*b*) may be utilized in connection with medication container 300. For example, the one or more sensors may include: one or more magnet and reed switches, one or more magnet and hall effect sensors, one or more optical sensors (e.g., infrared, visible light, or other), one or more pressure sensors (e.g., mechanical or solid state switch), one or more capacitance and/or capacitive touch sensors, one or more inductive touch sensors, one or more proximity sensors, and one or more electrical contacts.

Figures 4A, 4B:
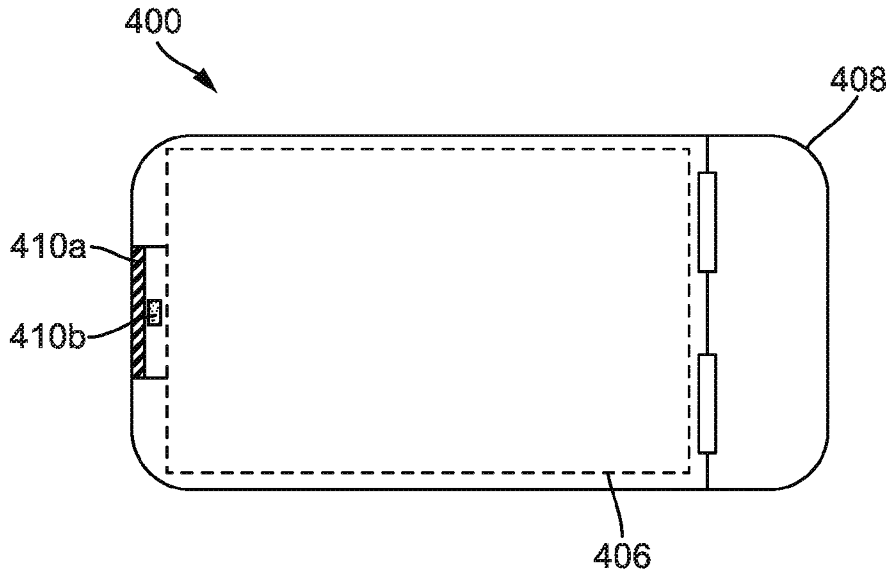

FIGS. 4A and 4B illustrate top and side views, respectively, of another exemplary embodiment of a medication container 400. Medication container 400 includes base 402 and top 404 coupled to the base (e.g., via a hinged connection) to permit top 404 to move from a first, closed position to a second, open position. Blister pack 406 may fit within medication container 400, and may be accessed by a user (e.g., patient) by moving top 404 from the first position to the second position. In some exemplary embodiments, top 404 may move relative to base 402 in a manner that resembles opening of a clam shell. In some exemplary embodiments, each of base 402 and top 404 may have a rectangular or generally rectangular shape, although other shapes (e.g., square or generally square, circular or generally circular) are possible. In some exemplary embodiments, each of base 402 and top 404 may be elongate and generally flat. In some exemplary embodiments, top 404 may be coupled via a hinge to base 402 along a short edge 408 of each of base 402 and top 404.

In some exemplary embodiments, medication container 400 may include one or more sensors (410*a*, 410*b*). In some exemplary embodiments, the sensor may include a first sensor component 410*a* and a second sensor component 410*b*. The sensor may detect that top 404 is open and/or closed relative to base 402. In some exemplary embodiments, sensor component 410*a* may be disposed within or on top 404, and sensor component 410*b* may be disposed within or on base 402. Medication container 400 may detect that a blister pack has been removed or is likely to have been removed in a state when top 404 is open and/or closed (e.g., detecting that top 404 is opened, or detecting that top 404 is open for some duration of time, and then closed).

In some exemplary embodiments, medication container 400 includes circuitry (e.g., one or more printed circuit boards and/or one or more printed circuit board assemblies 412) in communication with the one or more sensors (e.g., 410*a*, 410*b*). In some exemplary embodiments, medication container 400 includes a wireless circuit board that includes electronic components, e.g., a microprocessor, a wireless module, radio-frequency (RF) circuitry, and power circuitry. In some exemplary embodiments, the microprocessor may transmit, via a wireless antenna and to a server computer via a communication network. In some exemplary embodiments, the circuitry may be included in or on base 402. In other exemplary embodiments, the circuitry may be included in or on top 404. In still other exemplary embodiments, the circuitry may be included in or on both base 402 and top 404. Upon receipt of one or more outputs from the one or more sensors (e.g., one or more outputs indicating whether top 404 was opened and/or closed), the circuitry may store in memory of medication container 400 and/or transmit data indicative of whether medication has been or is likely to have been removed from the one or more blister packs.

In some exemplary embodiments, the one or more sensors (e.g., 410*a*, 410*b*) may be positioned and configured to detect whether the one or more blister packs have been removed. For example, the one or more sensors may detect a blister pack, then detect an absence of the blister pack as the blister pack is removed, and/or then detect the blister pack once again as the blister pack is returned to medication container 400. In some exemplary embodiments, the one or more sensor components may be disposed in or on base 402 and/or top 404. In some exemplary embodiments, at least one sensor component may be included in or on blister pack 406. For example, a sensor component may be located into or on a blister pack 406 or other medication package, by which a sensor component on medication container 400 may determine that blister pack 406 has been removed and/or returned, obtain information regarding the medication, e.g., type of medication, batch of medication, or dosage, and/or obtain other information (e.g., a medication regimen for a particular patient for which blister pack 406 is intended).

In some exemplary embodiments, one or more outputs of the one or more sensors may be indicative of one or more measurements, for example, of a quantity of medication in one or more blister packs 406.

Any suitable one or more sensors (e.g., 410*a*, 410*b*) may be utilized in connection with medication container 400. For example, the one or more sensors may include: one or more magnet and reed switches, one or more magnet and hall effect sensors, one or more optical sensors (e.g., infrared, visible light, or other), one or more pressure sensors (e.g., mechanical or solid state switch), one or more capacitance and/or capacitive touch sensors, one or more inductive touch sensors, one or more proximity sensors, and one or more electrical contacts.

Figure 5A:
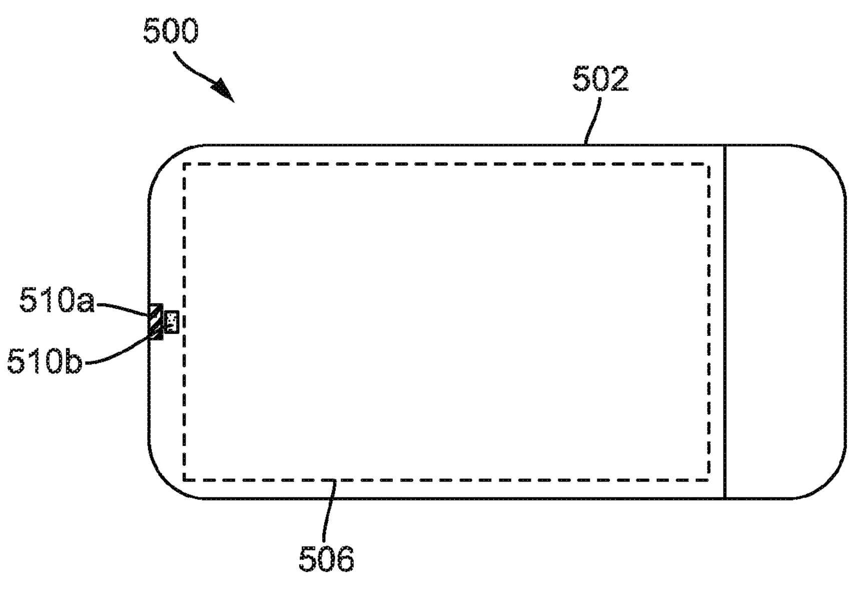
Figure 5B:
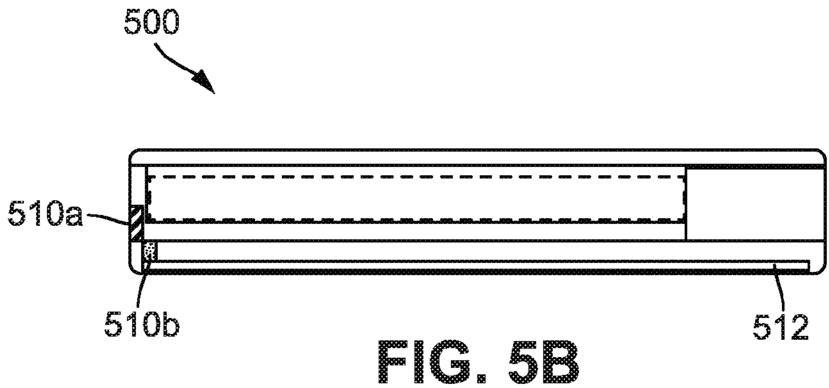
Figure 5C:
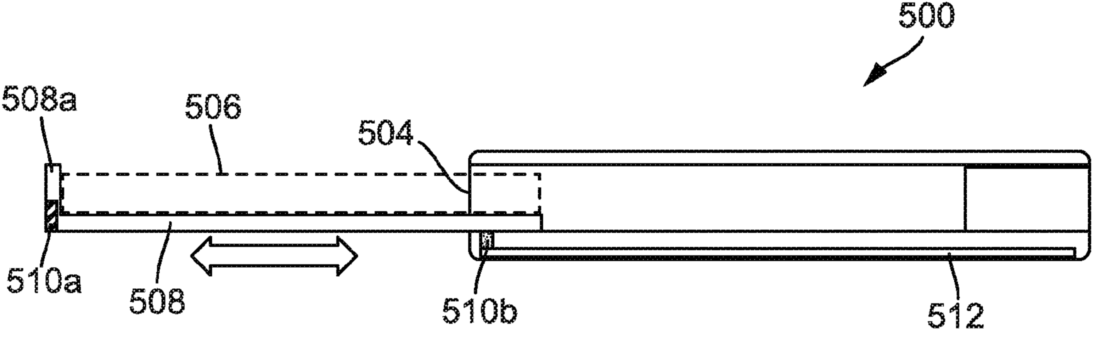

FIGS. 5A, 5B, and 5C illustrate top and side views of another exemplary embodiment of a medication container 500. Medication container 500 includes base 502 having an open end 504 (e.g., short end 504). Blister pack 506 may fit in or on tray 508, which may be configured to slide into and out of base 502. Blister pack 506 may be accessed by a user (e.g., patient) by sliding tray 508 in and out of open end 504 of base 502. In some exemplary embodiments, each of base 502 and tray 508 may have a rectangular or generally rectangular shape, although other shapes (e.g., square or generally square, circular or generally circular) are possible. In some exemplary embodiments, each of base 502 and tray 508 may be elongate and generally flat. In some exemplary embodiments, in a state when tray 508 is fully inserted within base 502 an end 508*a* of tray 508 covers open end 504 of base 502.

In some exemplary embodiments, medication container 500 may include one or more sensors (510*a*, 510*b*). In some exemplary embodiments, a sensor may include a first sensor component 510*a* and a second sensor component 510*b*. The sensor(s) may detect that tray 508 (which may or may not contain a blister pack 506) is inserted within and/or removed from base 502. In some exemplary embodiments, sensor component 510*a* may be disposed within or on tray 508. In some exemplary embodiments, sensor component 510*b* may be disposed within or on base 502.

In some exemplary embodiments, medication container 500 includes circuitry (e.g., one or more printed circuit boards and/or one or more printed circuit board assemblies 512) in communication with the one or more sensors (e.g., 510*a*, 510*b*). The circuitry may be disposed, for example, on or in a bottom and/or top surface of base 502. In some exemplary embodiments, medication container 500 includes a wireless circuit board that includes electronic components, e.g., a microprocessor, a wireless module, radio-frequency (RF) circuitry, and power circuitry. In some exemplary embodiments, the microprocessor may transmit, via a wireless antenna and to a server computer via a communication network. Upon receipt of one or more outputs from the one or more sensors (e.g., one or more outputs indicating whether blister pack 506 was inserted and/or removed), the circuitry may store in memory of medication container 500 and/or transmit data indicative of whether medication has been or is likely to have been removed from the one or more blister packs.

In some exemplary embodiments, the one or more sensors (e.g., 510*a*, 510*b*) may be positioned and configured (e.g., at or proximate to open end 504) to detect whether the one or more blister packs have been removed. For example, the one or more sensors may detect a blister pack, then detect an absence of the blister pack as the blister pack is removed, and/or then detect the blister pack once again as the blister pack is returned to medication container 500. In some exemplary embodiments, at least one sensor component may be included in or on blister pack 506. For example, a sensor component may be located into or on a blister pack 506 or other medication package. A sensor component on medication container 500 may determine that blister pack 506 has been removed and/or returned, obtain information regarding the medication, e.g., type of medication, batch of medication, or dosage, and/or obtain other information (e.g., a medication regimen for a particular patient for which blister pack 506 is intended).

In some exemplary embodiments, one or more outputs of the one or more sensors may be indicative of one or more measurements, for example, of a quantity of medication in one or more blister packs 506.

Any suitable one or more sensors (e.g., 510*a*, 510*b*) may be utilized in connection with medication container 500. For example, the one or more sensors may include: one or more magnet and reed switches, one or more magnet and hall effect sensors, one or more optical sensors (e.g., infrared, visible light, or other), one or more pressure sensors (e.g., mechanical or solid state switch), one or more capacitance and/or capacitive touch sensors, one or more inductive touch sensors, one or more proximity sensors, and one or more electrical contacts.

Figure 6A:
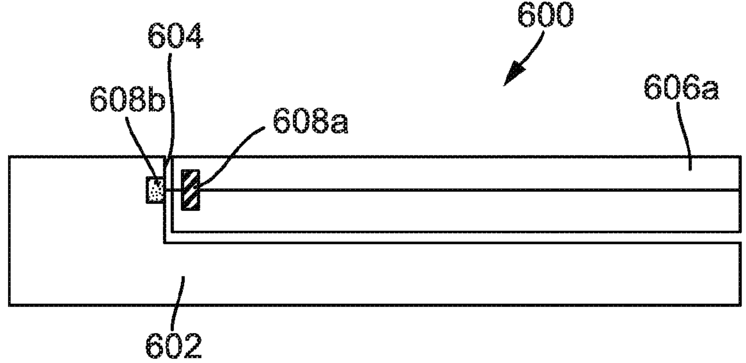
Figure 6B:
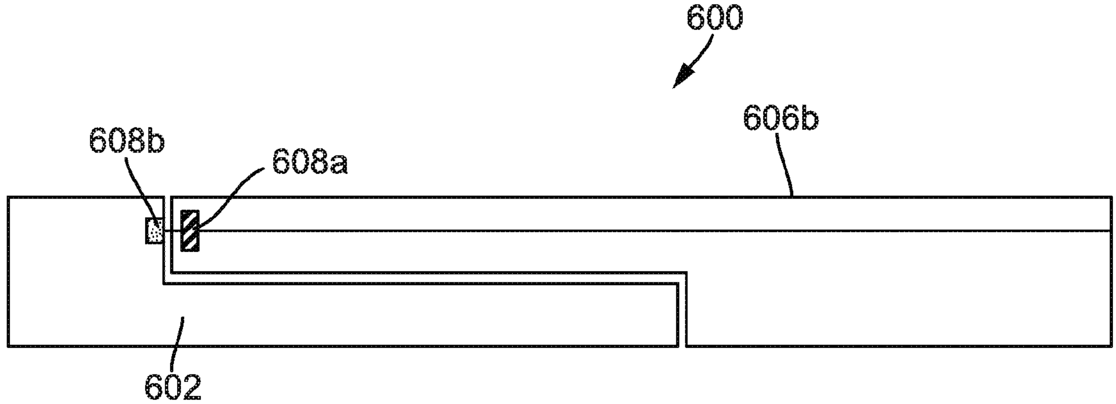

FIGS. 6A and 6B illustrate side views of another exemplary embodiment of a medication container 600. Medication container 600 includes base 602 having at least one surface 604 configured to couple to a blister pack (e.g., blister pack 606*a*, 606*b*). A blister pack (606*a*, 606*b*) may couple to medication container 600 via any suitable connection or coupling (e.g., via a friction fit or a snap fit), and may be accessed by a user (e.g., patient) by decoupling blister pack (606*a*, 606*b*) from base 602. In some exemplary embodiments, base 602 may have a rectangular or generally rectangular shape (e.g., along a bottom of the base 602), although other shapes (e.g., square or generally square, circular or generally circular) are possible. In some exemplary embodiments, base 602 may be elongate and generally flat (e.g., along the bottom of the base 602). In some exemplary embodiments, in a state when blister pack 606 is coupled to base 602, at least a portion of blister pack 606 may extend past an end of base 602. In some exemplary embodiments, base 602 may accommodate and couple to different sized blister packs (606*a*, 606*b*). In some exemplary embodiments, a modular device, as shown for example in FIGS. 6A and 6B, may be combined with any of the preceding exemplary embodiments shown and described in connection with FIGS. 1A, 1B, 2A, 2B, 3A, 3B, 4A, 4B, 5A, 5B, and 5C. The exemplary embodiments may be constructed to permit a modular base to fit, receive or couple to different sized blister packs.

In some exemplary embodiments, medication container 600 and/or a blister pack (606*a*, 606*b*) may include one or more sensors (608*a*, 608*b*). In some exemplary embodiments, a sensor may include a first sensor component 608*a* and a second sensor component 608*b*. The sensor(s) may detect that blister pack (606*a*, 606*b*) is coupled to and/or decoupled from base 602. In some exemplary embodiments, sensor component 608*a* may be coupled to a blister pack (606*a*, 606*b*) and sensor component 608*b* may be disposed within or on base 602.

In some exemplary embodiments, medication container 600 includes circuitry (e.g., one or more printed circuit boards and/or one or more printed circuit board assemblies) in communication with the one or more sensors (e.g., 608*a* and/or 608*b*). The circuitry may be disposed, for example, on or in a bottom and/or top surface of base 602. In some exemplary embodiments, medication container 600 includes a wireless circuit board that includes electronic components, e.g., a microprocessor, a wireless module, radio-frequency (RF) circuitry, and power circuitry. In some exemplary embodiments, the microprocessor may transmit, via a wireless antenna and to a server computer via a communication network. Upon receipt of one or more outputs from the one or more sensors (e.g., one or more outputs indicating whether blister pack (606*a*, 606*b*) was inserted and/or removed), the circuitry may store in memory of medication container 600 and/or transmit data indicative of whether medication has been or is likely to have been removed from the one or more blister packs.

In some exemplary embodiments, the one or more sensors (e.g., 608*a*, 608*b*) may be positioned and configured to detect whether the one or more blister packs have been coupled to and/or decoupled from base 602. For example, the one or more sensors may detect a blister pack, then detect an absence of the blister pack as the blister pack is removed, and/or then detect the blister pack once again as the blister pack is returned to medication container 600. A sensor component may be located into or on a blister pack (606*a*, 606*b*) or other medication package. A sensor component on medication container 600 may determine that blister pack (606*a*, 606*b*) has been removed and/or returned, obtain information regarding the medication, e.g., type of medication, batch of medication, or dosage, and/or obtain other information (e.g., a medication regimen for a particular patient for which the blister pack is intended).

In some exemplary embodiments, one or more outputs of the one or more sensors may be indicative of one or more measurements, for example, of a quantity of medication in one or more blister packs (606*a*, 606*b*).

Any suitable one or more sensors (e.g., 608*a*, 608*b*) may be utilized in connection with medication container 600. For example, the one or more sensors may include: one or more magnet and reed switches, one or more magnet and hall effect sensors, one or more optical sensors (e.g., infrared, visible light, or other), one or more pressure sensors (e.g., mechanical or solid state switch), one or more capacitance and/or capacitive touch sensors, one or more inductive touch sensors, one or more proximity sensors, and one or more electrical contacts.

Figure 7:
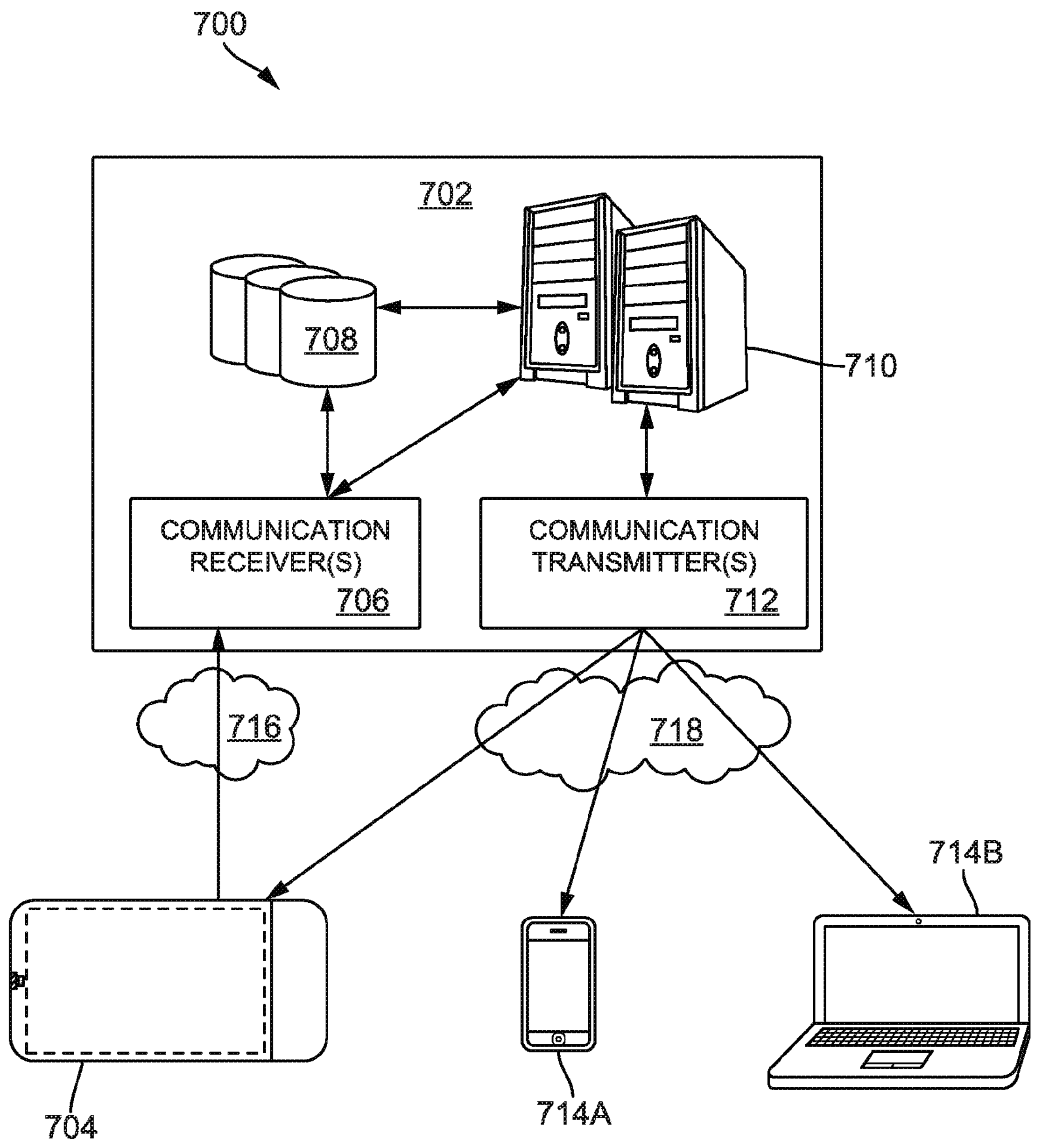
FIG. 7 illustrates a server computer that may communicate with circuitry on or in a medication container to generate reminders and/or alerts for a patient, a caregiver, a pharmacy, any other individual or entity, and/or any combination thereof according to an exemplary embodiment of the present disclosure.

FIG. 7 illustrates a system 700 including a server computer 702 that may communicate with the circuitry on a medication container 704 (e.g., medication container 100, 200, 300, 400, 500, 600, and/or 800) to generate one or more reminders and/or alerts for a patient, a caregiver, a pharmacy, any other individual or entity, and/or any combination thereof. The server computer 702 may include at least one communication receiver 706, at least one database 708, at least one programmable processor 2010 (FIG. 20), and at least one communication transmitter 712. The at least one programmable processor 2010 may be, in different exemplary embodiments, a processor, a microprocessor, a controller, a microcontroller, a data processor, a programmable data processor, and/or the like. In various exemplary embodiments, the server computer 702 may be in two-way communication with the medication container and/or one or more other computers (e.g., one or more computers 714A or 714B).

In various exemplary embodiments, the at least one communication receiver 706 of the server computer 702 may be configured to receive data via the first communication network 716 from circuitry on one or more medication containers described herein. The data may be, for example, data that corresponds to one or more measurements (e.g., binary detections) of one or more of the sensors described herein, e.g.: one or more sensor measurements indicating opening and/or closing of a cap of a medication container, sliding in or out of a tray, and/or timing data (e.g., via a timestamp) indicating a time of the opening and/or closing as identified by the one or more sensors or the one or more processors of the medication container; one or more sensor measurements indicating whether one or more blister packs and/or other cartridges is present within or coupled to the medication container (e.g., one or more measurement(s) indicating whether one or more blister packs have been inserted to and/or removed from the medication container) and/or timing data (e.g., via a time stamp) indicating a time of the insertion and/or removal the blister pack(s) as identified by the one or more sensors or the one or more processors of the medication container; and/or one or more sensor measurements indicating a quantity of medication within one or more blister packs and/or timing data (e.g., via a timestamp) indicating a time of the measurements as identified by the one or more sensors or the one or more processors of the medication container. Based at least in part on the receipt of the data, and/or other data (e.g., historical data stored by or otherwise accessible to the server computer in a database 708, e.g., data indicating one or more previous measurements received by the one or more sensors and/or timing data regarding timing of the measurements), the server computer including one or more processors 2010 (FIG. 20) may determine whether at least one criterion is satisfied and based on the determination trigger one or more reminders and/or alerts to a patient, a caregiver, and/or other entity (e.g., a pharmacy). For example, the alerts, which may include text, audio, imagery, video, or any combination thereof, may be transmitted to the medication container(s) themselves (e.g., medication containers 100, 200, 300, 400, 500, 600, and/or 800, each of which may include one or more alert devices, e.g., one or more speakers for audio alerts and/or one or more light emitting devices (e.g., LEDs) for visual alerts, activated in response to receipt of the alerts) and/or to other computing devices (e.g., computing devices, e.g., a patient's mobile phone 714A, laptop computer 714B, tablet computer, or other device, which may receive and display one or more messages, e.g., one or more SMS text messages or emails).

In some exemplary embodiments, the communication network may receive data from a medication container (e.g., medication container 100, 200, 300, 400, 500, 600, and/or 800) indicating that a patient has or is likely to have missed a dose of medication.

In one exemplary embodiment, the at least one communication receiver 706 may be configured to receive, via a first communication network 716 and from circuitry on a medication container 100, 200, 300, 400, 500, 600, and/or 800, data indicating that content within the one or more blister pack(s) was not withdrawn within a preset amount of time. For example, the data indicating that content within the one or more blister pack(s) was not withdrawn within the preset amount of time may indicate whether the blister pack(s) themselves are present and/or have been removed (e.g., a binary detection), as determined, for example, by one or more sensors configured to detect the presence or absence of one or more of the blister pack(s). Alternatively or additionally, the data indicating that content within the one or more blister pack(s) was not withdrawn within the preset amount of time may identify one or more specific amounts or quantities of contents with one or more blister packs (e.g., weight or quantity of liquid medication or pills), as determined, for example, by the one or more sensors configured to determine a weight or quantity within one or more blister packs. The at least one database 708 may be communicatively coupled to the at least one communication receiver 706. The at least one database 708 may be configured to store at least the received data. The at least one programmable processor 2010 (FIG. 20) may be communicatively coupled to at least one of (e.g., both of) the at least one communication receiver 706 and the at least one database 708. The at least one programmable processor 2010 may determine, upon or subsequent to the receiving of the data, whether at least one criterion is satisfied, the at least one programmable processor 2010 generating an alert in response to a determination that the at least one criterion is satisfied. The at least one communication transmitter 712 may be communicatively coupled to the at least one programmable processor 2010. The at least one communication transmitter 712 may be configured to transmit, via a second communication network 718, one or more alerts to a computing device 714 (e.g., a pharmacy computer) and/or the medication container 704 (e.g., medication container 100, 200, 300, 400, 500, 600, and/or 800).

The indication that content within the one or more blister packs was not withdrawn may indicate that a dose of medication contained within the blister pack(s) was missed or otherwise not removed or dispensed within the preset amount of time. Each computing device 714 is one of a desktop computer, a laptop computer, a tablet computer, a phablet computer, and a cellular phone. In one exemplary embodiment, the computing device 714 may be configured to be operated by a patient using the medication container 100, 200, 300, 400, 500, 600, and/or 800. In another exemplary embodiment, the computing device 714 may be configured to be operated by at least one of: a caregiver (e.g., hospital, clinician, doctor, nurse, technician, clinical staff member, and/or any other caregiver) treating a patient using the medication container 100, 200, 300, 400, 500, 600, and/or 800, a pharmacy authorized to provide medication to one or more patients, and a healthcare company authorized to obtain healthcare data of one or more patients. In one exemplary embodiment, the first communication network 716 may be same or substantially the same as the second communication network 718 (e.g., internet). In an alternate exemplary embodiment, the first communication network 716 may be different and separate from the second communication network 718. The first communication network 716 may be one or more of a local area network, a wide area network, internet, intranet, cellular network, Bluetooth network, infrared network, any other network, and any combination thereof. The second communication network 718 may be one or more of a local area network, a wide area network, internet, intranet, cellular network, Bluetooth network, infrared network, any other network, and any combination thereof.

Another exemplary embodiment of the present disclosure is directed to directly measuring the number of doses (e.g., pills) in a medication container, e.g., a pill bottle. For example, a direct manner to determine that a patient requires a refill is to measure how many pills are left within the medication container. Towards that end, the exemplary embodiment includes a capacitance sensor that returns values that vary with the number of doses in a medication container. Briefly, a capacitor is a non-linear electronic component that is capable of storing an electric charge. Traditionally, a capacitor contains two conductive plates separated by a material with determined dielectric properties. The material is chosen based on an ability of the material to store energy and determines the overall capacitance. A change in the material, e.g., material type or thickness, results in a change in capacitance. The exemplary embodiment includes an interdigital capacitor (IDC) to detect pills within a pill bottle, e.g., the pill bottle of FIG. 8A. An IDC is essentially a variable capacitor that changes in capacitance based on the material (type and quantity) that is resting above it. In some exemplary embodiments, IDCs are provided on a relatively small scale to detect fluidic properties (microfluidics), or large scale for binary presence detection (mechanical button replacements). An unexpected result includes a determination that an IDC sensor may be provided to detect discrete properties on a macro level (e.g., number of pills within a bottle). With experimentation, an IDC sensor may be deployed in order to overcome sources of error, e.g., electrical noise, temperature and humidity variations causing practical implementation extremely difficult. An exemplary embodiment of the present disclosure is illustrated in FIGS. 8A-14.

Figure 8A:
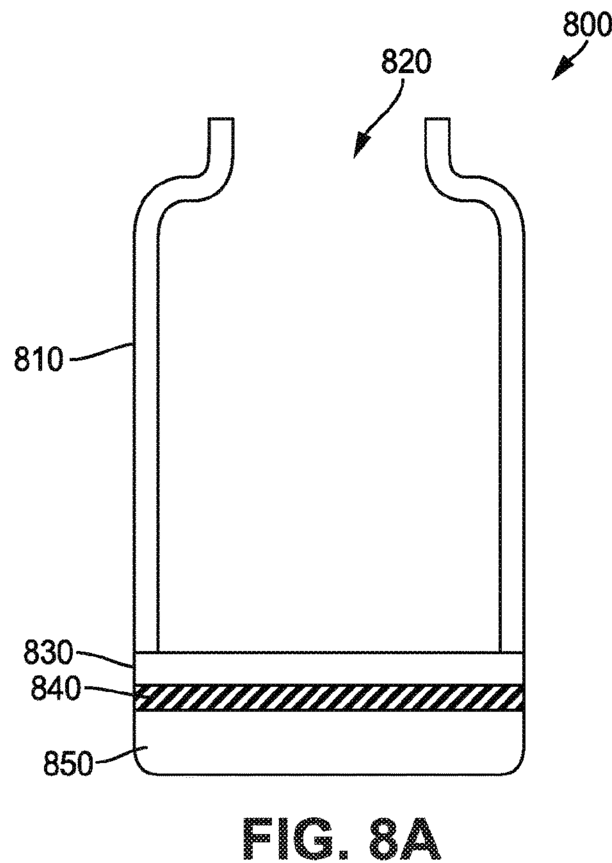
FIG. 8A illustrates a vertical cross section of a pill bottle with an interdigital capacitor (IDC) sensor according to an exemplary embodiment of the present disclosure.
Figure 8B:
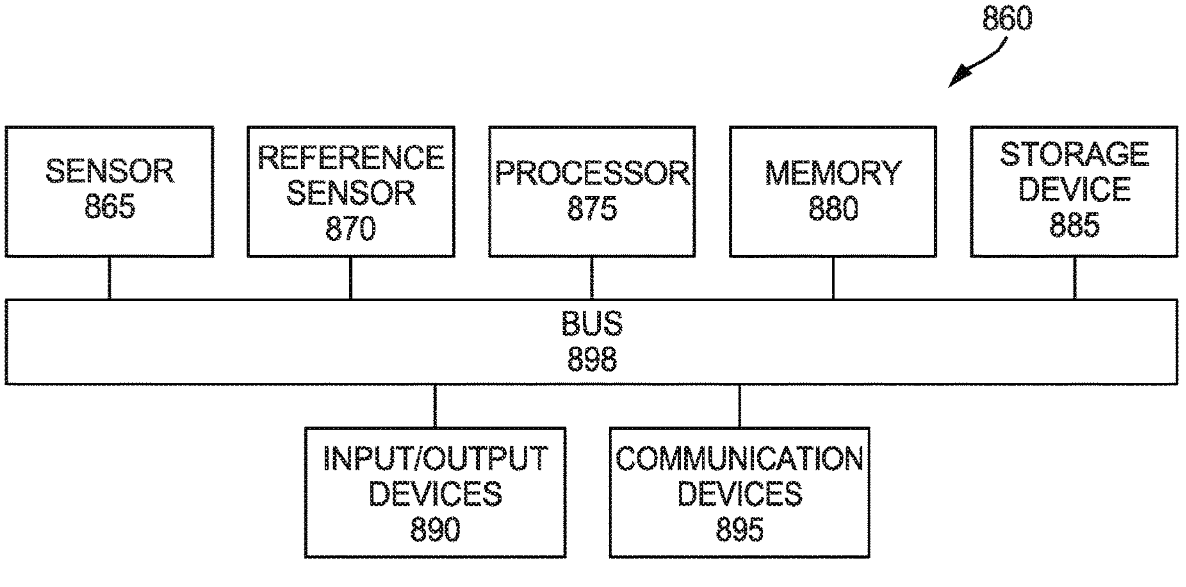
FIG. 8B illustrates the components of a system for identifying changes in the number of doses, or amount of medication, in a container, e.g., the container of FIG. 8A.

FIG. 8A illustrates a vertical cross section 800 of a pill bottle 810 with an interdigital capacitor (IDC) sensor. FIG. 8B illustrates the components of a system 860 for identifying changes in the number of doses, or amount of medication, in a container, e.g., the container of FIG. 8A. The pill bottle 810 includes a cavity 820 for storing pills. The bottom of the bottle 810 accommodates a printed circuit board assembly 840, protected by upper layer 830 and lower layer 850. The printed circuit board assembly 840 may include one or more of a sensor 865, a reference sensor 870, a processor 875, a memory 880, a storage device 885, input/output devices 890, communication devices 895, and bus 898. The sensor 865 and/or the reference sensor 870 may be an IDC sensor. In various exemplary embodiments, the sensor 865 may be printed on the top of the printed circuit board assembly 840, on the side of the pill cavity 820. The printed circuit board assembly 840 may have a shape that conforms to a cross-section of the internal cavity of the medication container 810.

The reference sensor 870 and processor 875 may be printed on the opposite side of the printed circuit board, on the side opposite the pill cavity 810, facing lower layer 850. The processor 875 may include a processing circuit and a microcontroller unit which may communicate with each other via a digital communication bus. For example, the processing circuit may transmit data from the IDC sensor 865 to the microcontroller (MCU) within the pill bottle via a digital communication bus 898 and/or a communication device 895.

The reference IDC sensor 870 may be smaller than the pill detection IDC sensor 865. The reference IDC sensor 870 changes capacitance with changes in temperature and humidity. The reference IDC sensor 870 may obtain reliable data, and the reliable data may offset the effects of temperature and humidity that cause data to drift. In various exemplary embodiments, the top (IDC sensor 865) and bottom (processing circuit 875 and reference IDC sensor 870) of the printed circuit board is separated by an internal conductive layer that is either floating or connected to ground to help focus the IDC detection range and reduce overall noise.

In various exemplary embodiments, memory 880 and/or storage device 885 stores temperature and/or humidity calibration factors, sensor 865 readings, reference sensor 870 readings, instructions for processor 875 to follow, and/or timing information. Input/output devices 890 and communication devices 895 may be provided to enter or offload data or instructions to and from medication container 800.

Figures 9A, 9B, 9C:
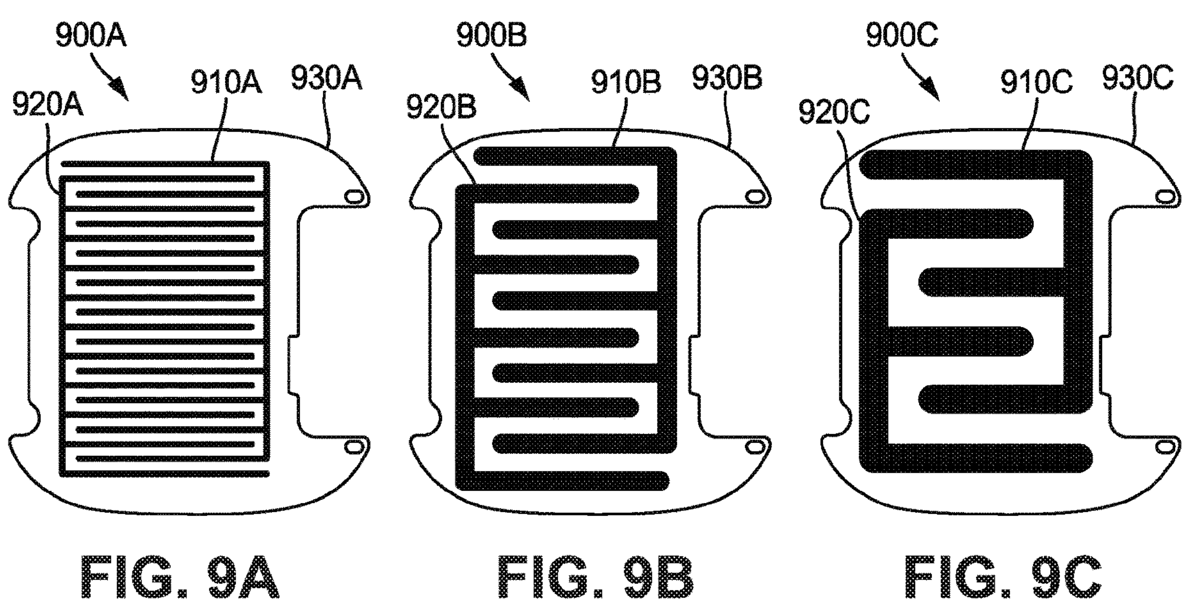
FIG. 9A illustrates an IDC sensor with narrow trace widths and narrow gaps according to an exemplary embodiment of the present disclosure.
FIG. 9B illustrates another IDC sensor with wider trace widths and wider gaps than the trace widths and gaps of the IDC sensor of FIG. 9A.
FIG. 9C illustrates another IDC sensor with wider trace widths and wider gaps than the trace widths and gaps of the IDC sensor of FIG. 9B.

FIG. 9A illustrates an IDC sensor 900A with narrow trace widths and narrow gaps. The sensor 900A may correspond to sensor 865, and/or reference sensor 870, of FIG. 8B. FIG. 9A shows right traces 910A and left traces 920A to form an interdigital capacitance sensor. The left traces 920A and right traces 910A come into proximity to each other, but do not intersect. The traces are analogous to fingers or digits; therefore capacitors that combine two sets of traces are referred to as interdigital capacitance (IDC) sensors. The left traces 920A and right traces 910A are printed on a circuit board 930A.

FIG. 9B illustrates another IDC sensor 900B with wider trace widths and wider gaps than the trace widths and gaps of the IDC sensor of FIG. 9A. The sensor 900B may correspond to sensor 865, and/or reference sensor 870, of FIG. 8B. FIG. 9B shows right traces 910B and left traces 920B, on circuit board 930B, to form an interdigital capacitance sensor. The left traces 920B and right traces 910B come into proximity to each other, but do not intersect.

FIG. 9C illustrates another IDC sensor 900C with wider trace widths and wider gaps than the trace widths and gaps of the IDC sensor of FIG. 9B. The sensor 900C may correspond to sensor 865, and/or reference sensor 870, of FIG. 8B. FIG. 9C shows right traces 910C and left traces 920C, on circuit board 930C, to form an interdigital capacitance sensor. The left traces 920C and right traces 910C come into proximity to each other, but do not intersect.

Figure 10:
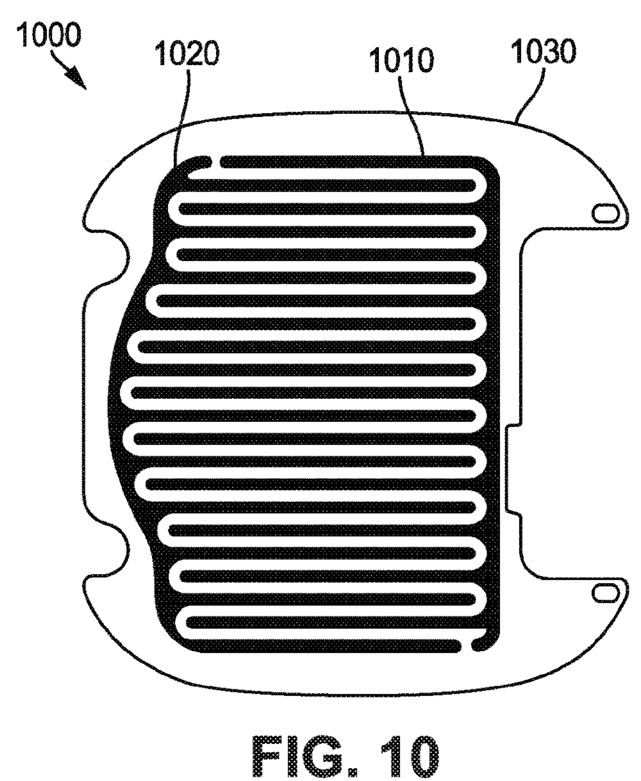
FIG. 10 illustrates an IDC sensor for placement in the bottom of the pill bottle of FIG. 8.

FIG. 10 illustrates an IDC sensor 1000 for location in the bottom of the pill bottle of FIG. 8A. The IDC sensor 865 provided to detect pills within the bottle cavity 920 may be optimized for pill size and material content. Drugs are usually in capsule or caplet form and are formulated with a small amount of active ingredient and a large amount of excipient. In some exemplary embodiments, the excipient may drastically outweigh the other material in the pill. In various exemplary embodiments, excipients of interest include lactose and magnesium stearate among others. To ensure optimum detection, the IDC may be designed such that the capacitance changes significantly each time a pill is added or removed, and is sensitive enough to detect changes at the top of the cavity (penetration depth). Trace width, trace gap, and trace shape are all variables that may be adjusted to optimize IDC performance. Analytical testing demonstrates that trace width and gap on the order of about 1 mm is optimal for exemplary pill sizes.

The processing circuit 875 may take various forms. The processing circuit may receive measurements from the IDC sensor 865 and/or IDC reference sensor 870 as an input and may output a value that corresponds to the IDC capacitance such that as the IDC capacitance changes, so does the output. Benchtop testing has revealed that changes to the IDC sensor in response to a single pill is on the order of a fraction of about 1 picoFarad (a fraction of about 1.0E-12 Farads). Therefore, the processing circuit may be suitably sensitive enough to detect the relatively small changes reliably.

In various exemplary embodiments, the processing circuit may consist of an integrated circuit (IC) designed to detect femtoFarad (about 1.0E-15 Farads) changes in capacitances. The IC may include any number of capacitor inputs (IDC sensors, for example) and may output data in analog or digital format, e.g., a half-duplex communication protocol including an inter-integrated circuit (I2C) or a full duplex communication protocol including a serial peripheral interface (SPI). The IC may have any number of settings that may be optimized based on the IDC properties, e.g., base capacitance value and sensitivity to changes in capacitance.

Figure 11:
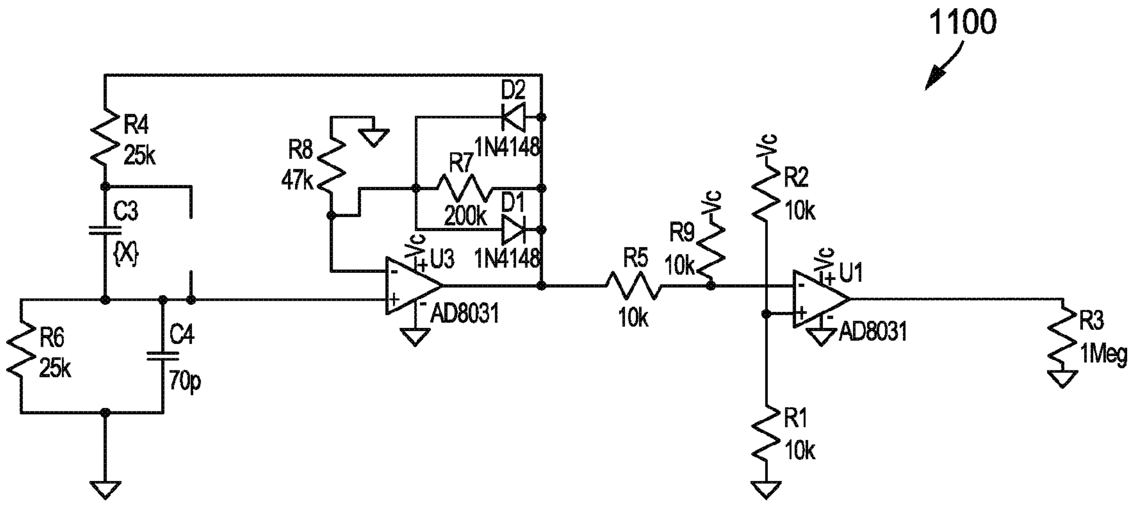
FIG. 11 is an example of a Wein bridge oscillator including an IDC sensor, e.g., one of the IDC sensors of FIG. 9A, 9B, 9C, or 10.

In various exemplary embodiments, the processing circuit is in the form of a variable oscillating circuit, e.g., a resonant circuit (RC), as depicted in FIG. 11. FIG. 11 illustrates a Wein bridge oscillator 1100, which may be provided. A sense capacitor C3 may be connected to form a variable frequency oscillator. The change in frequency may thus be measured. Alternatively, a root mean square (RMS) to direct current (DC) converter may be provided to detect changes in RMS values of the output that result from the change in frequency.

In some embodiments, the Wein bridge oscillator 1100 may include one or more capacitors, resistors, diodes, amplifiers, voltage controlled voltage sources, and grounds. For example, as shown in the exemplary embodiment of FIG. 11, the Wein bridge oscillator 1100 may include the following: the sense capacitor C3 operable at a capacitance X; a capacitor C4 operable at a capacitance of about 70 pF; a first resistor R1 operable at a resistance of about 10 kΩ; a second resistor R2 operable at a resistance of about 10 kΩ; a third resistor R3 operable at a resistance of about 1 MΩ; a fourth resistor R4 operable at a resistance of about 25 kΩ; a fifth resistor R5 operable at a resistance of about 10 kΩ; a sixth resistor R6 operable at a resistance of about 25 kΩ; a seventh resistor R7 operable at a resistance of about 200 kΩ; an eighth resistor R8 operable at a resistance of about 47 kΩ; a ninth resistor R9 operable at a resistance of about 10 kΩ; a first 1N4148 diode D1 operable at a voltage of about 75 V and an amperage of about 150 mA; a second 1N4148 diode D2 operable at a voltage of about 75 V and an amperage of about 150 mA; a first AD8031 amplifier U1 operable at a voltage of about 2.7 V, an amperage of about 800 μA, and a frequency of about 80 MHz; a third AD8031 amplifier U3 operable at a voltage of about 2.7 V, an amperage of about 800 μA, and a frequency of about 80 MHz; four voltage controlled voltage sources Vc; and six signal/low noise grounds.

Figure 12:
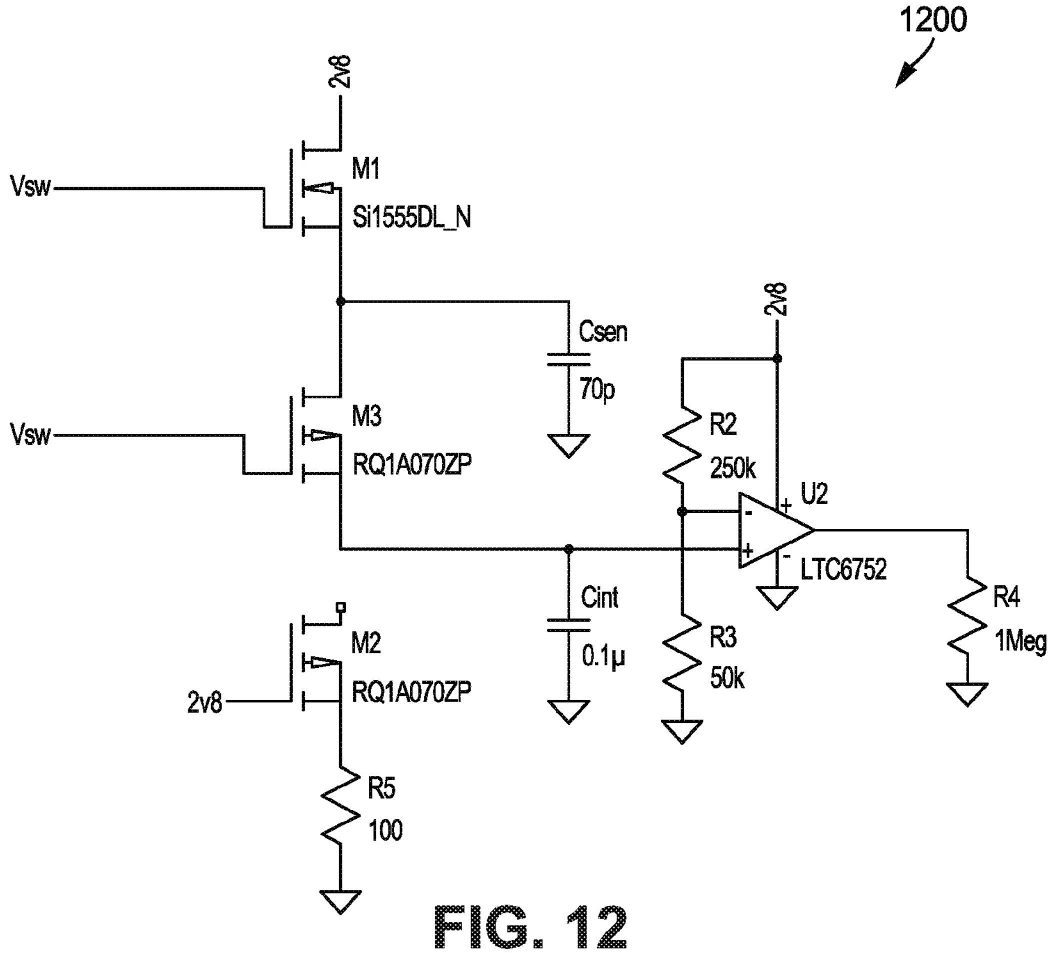
FIG. 12 is an example of a switched capacitor circuit including an IDC sensor, e.g., one of the IDC sensors of FIG. 9A, 9B, 9C, or 10.

Other exemplary embodiments may use a switched capacitor design for processing circuit 875, e.g., the switched capacitor circuit 1200 of FIG. 12, where Csen is the IDC sensor 865. In the circuit, a DC voltage is provided to fully charge the IDC capacitor. The DC source for charging the IDC capacitor is then disconnected followed by immediately connecting the IDC capacitor to another capacitor that is significantly larger in capacitance (greater than 10 times), which partially charges the second capacitor. The charging process is repeated until the second capacitor is fully charged. A comparator on the output of the second capacitor may then be provided to determine that the second capacitor is fully charged and the time required to reach full charge may be computed. Based on the capacitance of the IDC capacitor, the time required to charge the second capacitor varies enabling the ability to determine changes in the IDC capacitor.

In some embodiments, the switched capacitor circuit 1200 may include one or more capacitors, resistors, comparators, voltage controlled switches, current sources, metal-oxide-semiconductor field-effect transistors (MOSFETs), and grounds. For example, as shown in the exemplary embodiment of FIG. 12, the switched capacitor circuit 1200 may include the following: a switched capacitor Csen operable at a capacitance of about 70 pF; an integrating capacitor Cint operable at a capacitance of about 0.1 μF; a resistor R2 operable at a resistance of about 250 kΩ; a resistor R3 operable at a resistance of about 50 kΩ; a resistor R4 operable at a resistance of about 1 MΩ; a resistor R5 operable at a resistance of about 100Ω; an LTC6752 comparator U2 operable at a toggle rate of 280 MHz and a propagation delay of about 2.9 ns; two voltage controlled switches Vsw; three current sources **2*v*8 operating at a voltage of about 2.8 V; an Si1555DL_N complementary low-threshold MOSFET M1; an RQ1A070ZP 1.5 V p-channel MOSFET M2; an RQ1A070ZP 1.5 V Drive p-channel MOSFET M3**; and six signal/low noise grounds.

Figure 13:
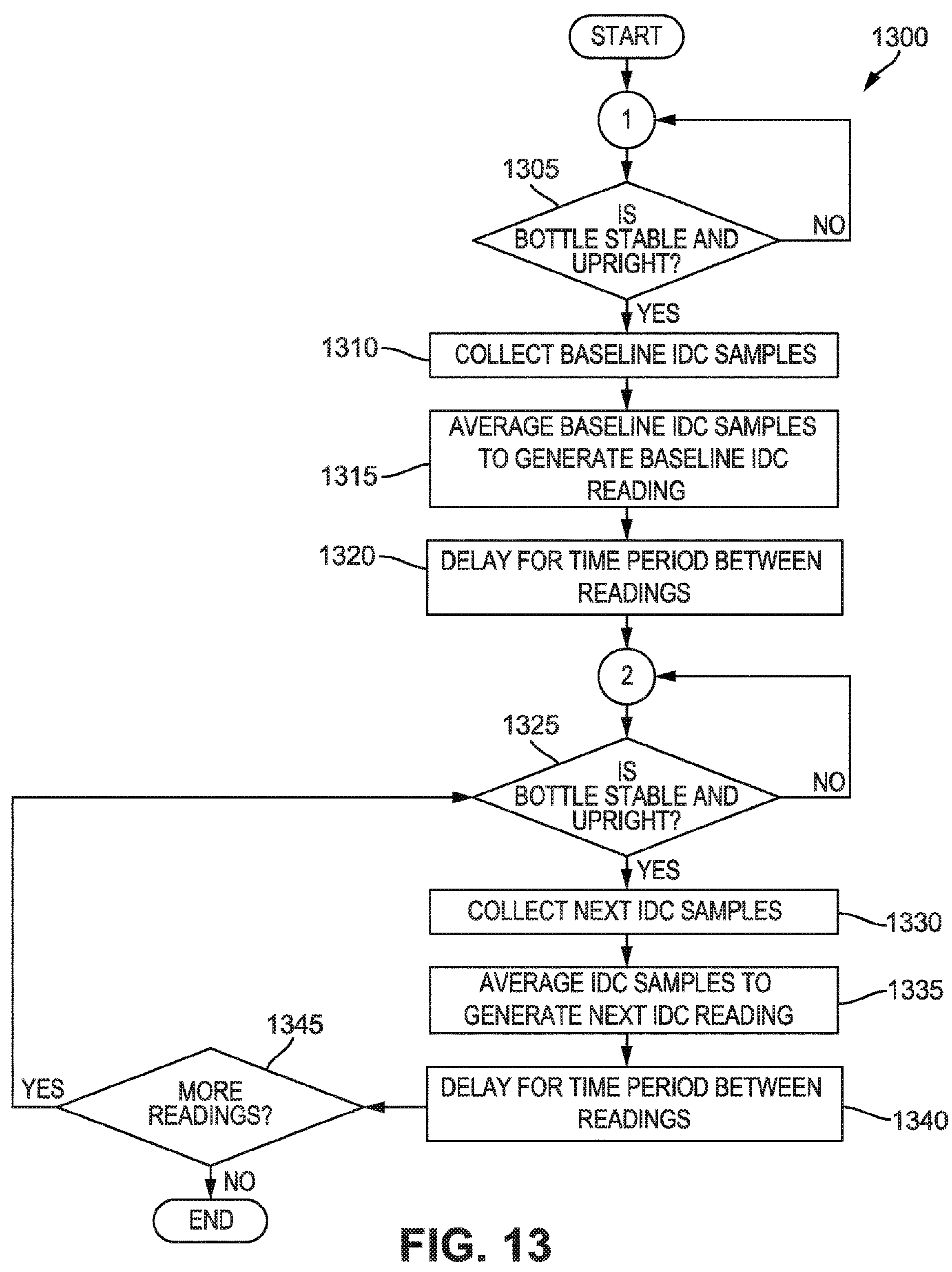
FIG. 13 is a method for collecting IDC sensor data according to an exemplary embodiment of the present disclosure.

FIG. 13 is a method 1300 for collecting IDC sensor data. One or more steps of the methods described herein may be executed by a controller. Method 1300 includes steps to address variations in sensor capacitance due to medication container movement, medication container orientation, changes in temperature, and changes in humidity. In response to a patient picking up or moving a medication container, pills within the medication container may move and change the IDC sensor 865 capacitance. In response to a determination that a bottle is not upright, some of the pills may be redistributed within the pill cavity 820, causing changes in the IDC sensor 865 capacitance. Further, IDC sensor 865 capacitance may vary with changes in temperature and/or humidity.

In step 1305, method 1300 determines whether the medication container is stable (stationary) and upright. Step 1305 may utilize one or more sensors, including an accelerometer, to measure the presence or absence of movement, as well as orientation, of the medication container. In response to a determination that the bottle is not stable and upright, method 1300 may return to 1305 until the medication container is stable and upright. In response to a determination that the bottle is stable and upright, the method 1300 moves to step 1310.

In step 1310, method 1300 collects a series of baseline IDC samples. For example, 10 samples may be obtained about 2 seconds apart. The number of samples and time between samples may vary in different exemplary embodiments. After collecting a series of samples, the method 1300 moves to step 1315.

In step 1315, method 1300 averages the baseline IDC samples to generate a baseline IDC reading. Collecting and averaging a series of samples helps eliminate noise. In various exemplary embodiments the standard deviation of a set of samples may be provided to identify and remove outliers. After averaging the samples, the method 1300 moves to step 1320.

In step 1320, method 1300 delays for a time period between readings. The delay between readings may vary based on how frequently doses should be administered by the patient. The delay between readings, may, for example, be about 30 minutes, about 60 minutes, or about 2 hours. At the end of the delay, the method 1300 moves to step 1325.

In step 1325, method 1300 determines whether the medication container is stable and upright, as was done in step 1305. Step 1325 may use one or more sensors, including an accelerometer, to measure the presence of absence of movement, as well as orientation, of the medication container. In response to a determination that the bottle is not stable and upright, method 1300 may return to step 1325 until the medication container is stable and upright. In response to a determination that the bottle is stable and upright, the method 1300 moves to step 1330.

In step 1330, method 1300 collects a series of additional IDC samples. For example, 10 samples may be obtained about 2 seconds apart. The number of samples and time between samples may vary in different exemplary embodiments. After collecting a series of samples, the method 1300 moves to step 1335.

In step 1335, method 1300 averages the baseline IDC samples to generate an additional IDC reading. Collecting and averaging a series of samples helps eliminate noise. In various exemplary embodiments the standard deviation of a set of samples may be provided to identify and remove outliers. After averaging the samples, the method 1300 moves to step 1340.

In step 1340, method 1300 delays for a time period between readings. The delay between readings may vary based on how frequently doses should be administered by the patient. The delay between readings, may, for example, be about 30 minutes, about 60 minutes, or about 2 hours. At the end of the delay, the method 1300 moves to step 1345.

In step 1345, method 1300 determines whether to take more readings. In response to a determination that more readings are required, the method 1300 moves to step 1325.

In various exemplary embodiments, data collected by method 1300 may be transmitted by communication device 895 to server 702 for additional processing, e.g., off-line processing. The off-line processing conserves battery life in the medication container. As noted above, the raw IDC data drifts with changes in temperature and humidity. Accordingly, data from the reference IDC sensor 870 is provided to adjust IDC sensor 865 reading. The adjustment is done by determining a baseline ratio of the sensor 865 and reference sensor 870, and adjusting both sets of data to allow the data to be unitless. Allowing the data to be unitless effectively calibrates or corrects the sensor 865 data for variations in temperature and humidity using reference sensor 870 data. The calibration or correction permits the two sets of data to be provided in conjunction for manipulation.

Figure 14:
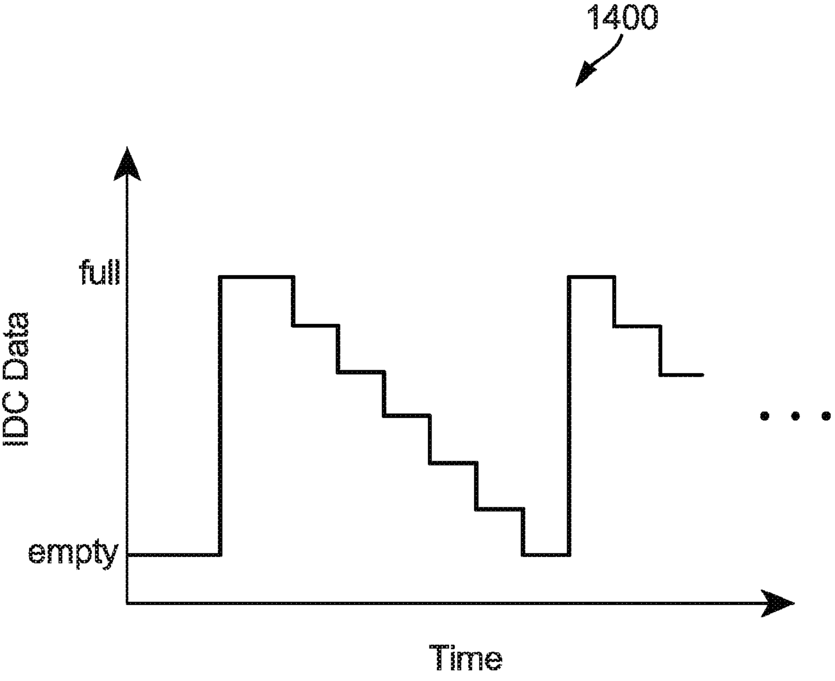
FIG. 14 is a graph illustrating IDC data as doses of medication are removed from or added to a medication container, e.g., the containers of any of FIGS. 1A, 1B, 2A, 2B, 3A, 3B, 4A, 4B, 5A, 5B, 5C, 6A, 6B, and 8A.

FIG. 14 is a graph illustrating IDC data as doses of medication are removed from or added to a medication container, e.g., the containers of any of FIGS. 1A, 1B, 2A, 2B, 3A, 3B, 4A, 4B, 5A, 5B, 5C, 6A, 6B, and 8A. FIG. 14 starts with an empty bottle. The IDC data takes a stepwise increase in response to filling of the bottle. As doses are removed, the IDC data decreases in a stepwise fashion. After the bottle is empty, the bottle may be filled again and doses removed. To determine that a patient is in need of a refill, a number of algorithms may be provided. In the instance the data is sufficiently linear, a linear regression analysis may be provided to determine that the data reaches some percent of the baseline value, then a determination may be made that a refill is needed. In another instance, in a state when the data is more parabolic than linear, a polynomial regression may be provided.

In other instances, the IDC data may exhibit a general trend (increasing or decreasing), but may not be reliable enough to make decisions based solely on one dimensional regressions. In particular, pattern recognition and predictive algorithms may be leveraged. With additional inputs, machine learning models may be leveraged to predict that a refill is needed, and to determine a time associated with the needed refill. Specifically, a neural network—that receives inputs including the IDC data, time elapsed, and an indicator of a state when the pill bottle cap is open and closed—may be provided for a model that predicts and decides that a patient is in need of a refill, and may determine a time associated with the needed refill. Additional inputs and alternative models may also be provided.

Providing a capacitive sensor within a pill bottle may be expanded to other form factors as well. Specifically, a solution with multiple capacitive sensors in a housing meant to store a blister pack or weekly pill case is another feasible solution. In the form factor of the housing meant to store the blister pack or weekly pill case, a printed circuit board may contain a multitude of individual capacitive sensors aligned with the pills in each cavity and may be provided to determine removal or non-removal of individual pills.

FIGS. 15-19 illustrate methods for processing container data by a central processor in, for example, a container 100, 200, 300, 400, 500, 600, and/or 800, a server 702, a mobile phone 714A, a laptop 714B, or by another computing device networked to, or in receipt of, container data, including one or more data providers that are in communication with the central processor via a digital communication network. One or more steps of the methods described herein may be executed by a controller. The one or more data providers may include patients, health care providers (HCPs), and/or physical containers for containing and monitoring medication, and which may be provided with sensors, one or more processors, one or more transceivers, and a battery for providing charge to the sensors, processors, and/or transceivers. The central processor may include one or more data processors for executing one or more computer-implemented programs, including artificial intelligence programs, natural language processing programs, and/or data analytics programs, or any combination thereof.

The central processor may include one or more data processors at a central location, e.g., with a central repository or database. However, the central processor may also be a distributed processor, with multiple processors distributed among multiple computing systems, e.g., server computers, or across a diverse geographical area, e.g., in a distributed computing system or distributed server system.

In accordance with some exemplary embodiments, the system receives data from multiple data providers or data sources. For example, the system may include a physical container, which includes a battery and one or more sensors for generating data, including, but not limited to: a determination that a patient opens the container to access and take their medication; a measurement of the contents of the container; a temperature (particularly proximate the container); an orientation of the container, e.g., by an accelerometer, or from a geographical information device e.g., the Global Positioning System (GPS); cellular connectivity, e.g., via one or more adjacent wireless carriers or wireless connectivity devices; and, battery power, as sensed and indicated by sensors associated with the container.

In some exemplary embodiments, a system is configured to receive data from patients and/or their representative directly, or via a communication network, which may be direct or indirect, i.e., through an intermediary, e.g., another person or computer. For example, the system may include a short messaging system (SMS) or multi-media messaging system (MMS) receiver for receiving text or multimedia messages, respectively. Alternatively, or in addition, the system may include a cellular transceiver for receiving cellular radio signals from a cellular radio. Thus, a patient or other data provider may use any of the above-mentioned data networks to transmit messages or calls to the system to provide data for receipt by the system.

In accordance with exemplary embodiments, the system may be configured as a secure system. Accordingly, in some exemplary embodiments, the system may be compliant with the Health Insurance Portability and Accountability Act (HIPAA) of 1996, which was created to modernize the flow of healthcare information, stipulate how Personally Identifiable Information (PII) maintained by the healthcare and healthcare insurance industries should be protected from fraud and theft, and address limitations on healthcare insurance coverage. For example, each container, e.g., a bottle, may transmit measurement data without patient-specific information. Each bottle/container may be associated with a specific patient by a code or other encoding scheme, or by encrypted data that is not viewable by the public. Further, all data may be stored securely in a HIPAA-compliant cloud storage, e.g., a secure database or the like, which has been approved by a government agency for compliancy with data restrictions.

The system may also receive data, either directly or from one of a number of application programming interfaces (APIs) e.g., representational state transfer (REST) APIs, from pharmacies, HCPs, and/or other parties, some of whom manually input data into their local systems or directly into the system. In some exemplary embodiments, the system may further include a patient-facing application ("app"), e.g., an app on a smart phone or portable computer. Some or all of the data collected, and results of the algorithms executed thereon, may interface with a patient-facing app to deliver information to patients. In some exemplary embodiments, the app may generate one or more graphical user interfaces (GUIs) for presenting the information to the patient. In other exemplary embodiments, the app may generate a signal, e.g., a tactile signal like a vibration or an audible signal, or a text message, or a graphical signal, e.g., a flashing light emitting diode (LED), or signaling screen or display, to represent at least some of the information presented to the patient.

Upon receipt of the data, the system may process the data to determine whether a dose was administered or missed, which in turn may be configured to execute automated interventions to the patient or their caregiver or pharmacy. The automated interventions may take the form of an audible signal, a visual signal, a text message, a graphical display, or the like. The automated interventions may include, without limitation, reminders, questions, targeted care (and a detailed description thereof), automated reports to HCPs, suggesting further patient intervention. The system may further process the data to determine that refills are needed, and a time for the needed refill, which may be configured to execute automated reports to HCPs, suggesting further patient intervention. The system may further process the data to determine which patients may need additional care due to a number of different possible issues (e.g., health issues, body temperature, qualitative measurements, side effects, payment, confusion and the like), which may be configured to execute triggers to HCPs, suggesting further patient intervention. In yet other exemplary embodiments, the system may further process the data to determine patient sentiment and patient experience, which may be configured to execute improved care programs and support to patients.

The system, and methods performed thereon, may be configured to execute a number of algorithms to improve processing of data from multiple sources, to improve compliance or adherence by a patient with a medication regiment or prescription for taking medication. The algorithms may be implemented or instantiated as one or more computer processes or programs, and may implement an algorithm that may reliably estimate, without limitation, the following: a determination that patients will likely drop off of the medication; a determination that patients will need a specific intervention; and a determination that patients may have a side effect. Further, the algorithms may be configured to reliably process patient messages configured to execute action, which increases adherence, and/or predict the impact of schedule changes on future adherence.

Figure 15:
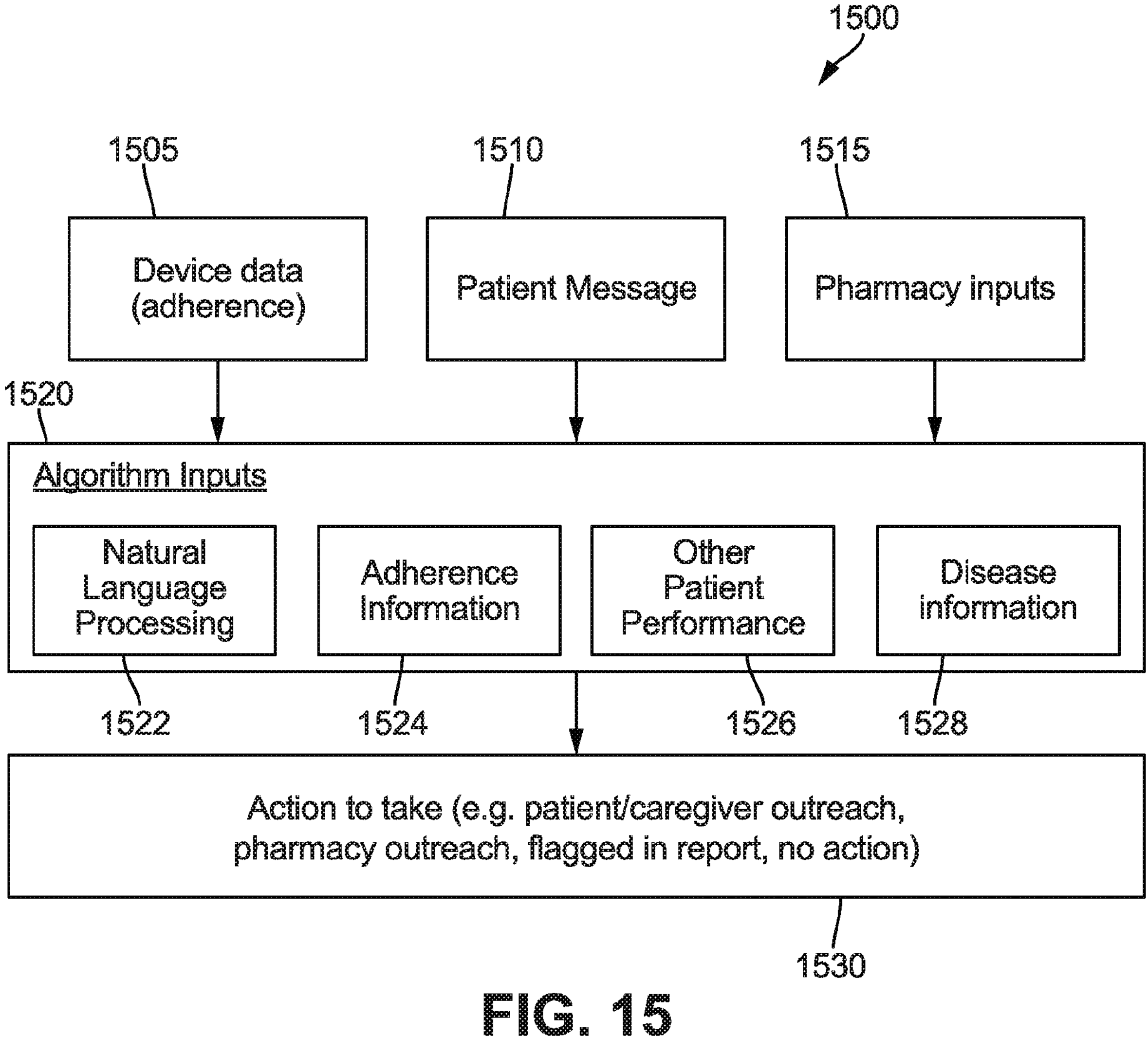
FIG. 15 shows a process flow diagram for determining an action to take, e.g., patient/caregiver outreach, pharmacy outreach, flagged in report, or no action according to an exemplary embodiment of the present disclosure.

In some exemplary embodiments, as shown in FIG. 15, a system may include a patient retention prediction module 1500. The patient retention prediction module 1500 may be implemented as an executable computer program that uses a model to predict or analyze certain patient behaviors, based on data received related to the patient, e.g., patient messages 1510, adherence device data 1505 from a container of medication accessed by the patient, and/or an HCP and/or pharmacy inputs 1515 from a pharmacist or pharmacy computer. Other inputs 1520 may include, without limitation, a natural language processing module 1522, adherence information (e.g., from the container) 1524, other patient performance data 1526 (from a variety of sources, including the patient themselves), and disease or condition information 1528, which may be obtained from a database or other online resource, for example.

The model to predict or analyze certain patient behaviors analyzes, and provides data for generating an output representing, e.g., the patient's dosing history, a time the doses were administered with respect to their scheduled dose time or a determination that the doses were missed, and a frequency and pattern of doses administered and missed. The scheduled dose time may be based on time of day (e.g., hourly, morning, evening, etc.), units/period, e.g., how many times per day, and periodicity. The model further analyzes, and provides data for generating an output representing, scheduled stoppages due to health, personal, doctor, or other issues. The model may further be provided to generate patient messages. The patient messages may be augmented by an artificial intelligence (AI) module, which operates on data generated by the model. The model may further be provided to generate additional data from pharmacy input. The model may be configured to then predict that patients may be dropping off or stopping the medication and a time for the predicted drop off or stoppage. Action 1530 may be configured to avoid patient drop-offs, e.g., patient or caregiver outreach, pharmacy outreach, or flagged in reporting.

In accordance with other exemplary embodiments, one or more algorithms may be configured for use by the system to receive and parse messages the patients send in or transmit. In some exemplary embodiments, the system uses natural language processing (NLP) trained on received patient messages to classify messages into different "buckets" or classifications of messaging, e.g., without limitation: in need of refill; in need of intervention by another party; experienced a side effect; in need of pharmacy support; or other actionable groupings or classifications.

Figure 16:
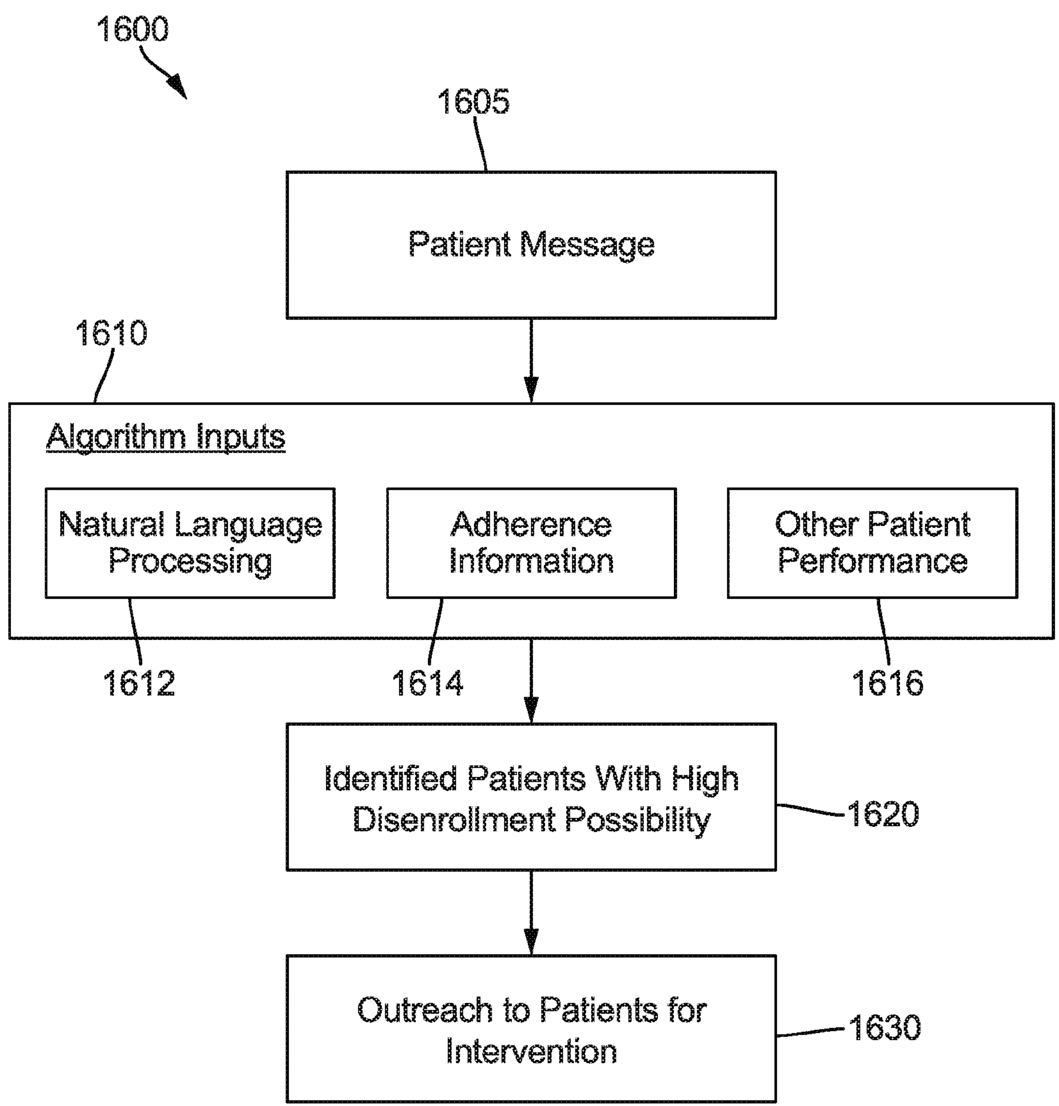
FIG. 16 shows a process flow diagram for identifying patients with a high disenrollment probability and outreach to patients for an intervention according to an exemplary embodiment of the present disclosure.

In some exemplary embodiments, and based on an algorithm 1600 as shown in FIG. 16, a time during the patient's treatment history that the patient messages 1605 were transmitted is recorded or logged, and processed to contextualize the information. Algorithm inputs 1610 may be obtained using natural language processing of the patient message 1612, adherence information 1614, and/or other patient performance information 1616. With the data (e.g., the time during the patient's treatment, the inputs 1610, the adherence information 1614, and/or the other patient performance information 1616), patients may be classified in one or more groups as to a likeliness to disenroll 1620, and may be assigned a probability of disenrollment. The probability may be generated as a score. Using the algorithm, the patients may be contacted by the system in response to a determination that a threshold of disenrollment probability is reached; interaction with the patient may be changed, modified or altered; the patient may be prompted to reach out to the patient's doctor; and the patient be prompted to provide feedback on whether or not the prediction was correct. Using the responses, the system updates the model to be more accurate in the future. In some exemplary embodiments, variables or inputs to the model may be applied with a weighting or value scheme, where some inputs are weighted more heavily than others, to continually train the model and make the model more effective.

In some alternative exemplary embodiments an algorithm may be provided for prediction of dose missing and/or patient intervention. Accordingly, an algorithm may be configured to predict that the patients are likely to miss an additional dose, to predict a time associated with the predicted missing the additional dose, to identify potentially at-risk patients, and to generate an interaction protocol for contacting the at-risk patients 1630 and improving their adherence.

Figure 17:
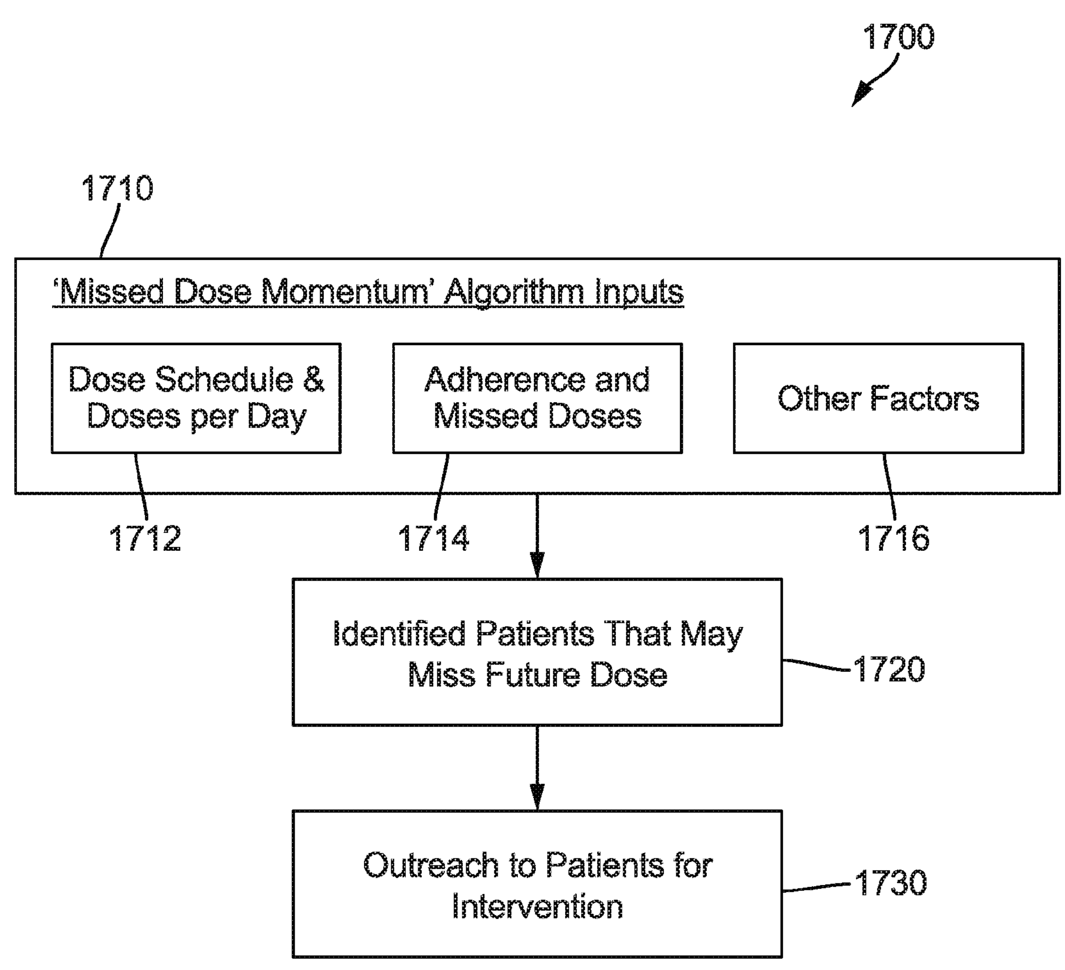
FIG. 17 shows a process flow diagram for identifying patients that may miss a future dose, and for outreach to patients for an intervention according to an exemplary embodiment of the present disclosure.

In some exemplary embodiments, as shown in FIG. 17, an algorithm may be implemented as a method 1700, with inputs for dose schedule and doses per day 1712, adherence and missed dose information 1714, and other factors 1716. A "Missed Dose Momentum" is defined as a frequency and/or a prevalence of missed doses. The doses may be prescribed by an HCP, a pharmacy, or the like. The algorithm takes into account the patient's dose schedule, which may be based on the number of a patient's doses per day 1712. The method uses a missed dose momentum and tags patients who reach the threshold of missed dose momentum as patients who are at risk of missing an additional dose 1720.

After taking into account previous outreach programs, the status of the patient, and a status of the container or bottle that contains the medication doses, patient outreach for intervention 1720 by, for example, a call or text message may be scheduled and transmitted. The call or the text message may provide information that may help the patient increase adherence. The missed dose momentum indicator is accurate in predicting that the patient will miss an additional dose, and the time associated with the predicted missing the additional dose. The missed dose momentum indicator may be provided to prevent an additional missed dose. The system as shown in FIG. 17 is effective in raising adherence in patients overall.

Figure 18:
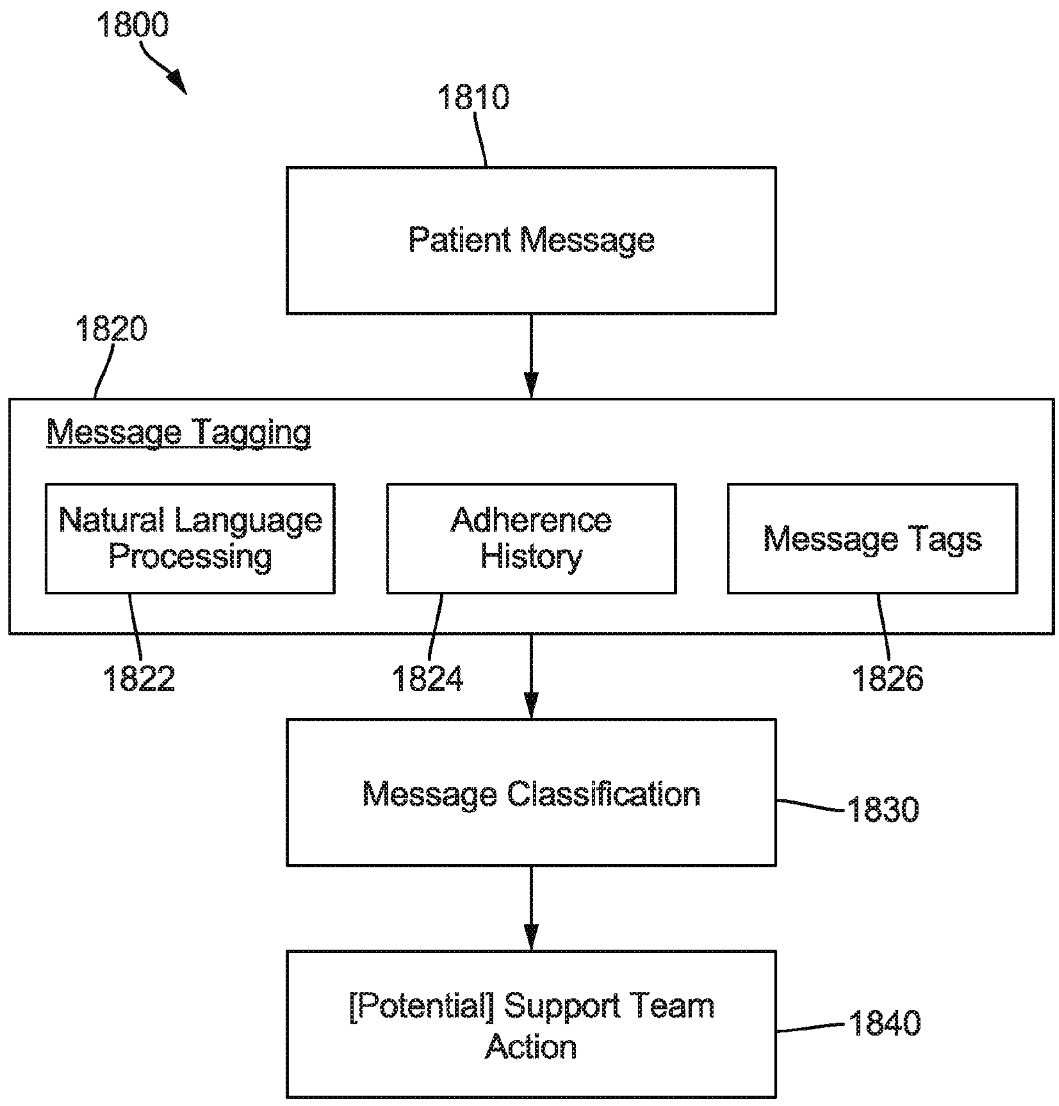
FIG. 18 shows a process flow diagram for message classification and potential support team action according to an exemplary embodiment of the present disclosure.

In some exemplary embodiments, as shown in FIG. 18, an algorithm may be implemented as a method 1800 to determine adherence impact based on schedule and/or medication changes. In accordance with the exemplary embodiments, an algorithm may be executed by the system to let pharmaceutical companies, pharmacies, or HCPs get key performance indicators (KPIs) of their patients by different cohorts. The model shown in FIG. 18 also predicts how schedule and medication changes will impact patient adherence by selecting different variables, e.g., schedules, etc. The method 1800 receives a patient message 1810, and includes message tagging 1820 inputs from natural language processing 1822 of the patient message, the patient's adherence history 1824, and message tags 1826.

Patients and patient messages may also be classified 1830 by different characteristics of their treatment. For example, a client may choose the patient's schedule, their time in program, doses per day, the dose strength, the side effect profile, disease progression, age, and/or gender. Regardless of the actual drug, the factors may predict a patient's adherence statistics, and the model may estimate the effect using the system will have on different pills and different schedules. The algorithm may be provided for future drug development and prediction of patient performance in the future.

Furthermore, side effects from medications may be predicted by comparing different dosing patterns from one or more patients. By collecting and storing patient dose strength and schedule, the system may determine which patients are more likely to get side effects than others. Then, by matching missed doses and pauses in the past, the system may predict that a patient is likely to have a side effect or a treatment change, and a time associated with the predicted side effect or treatment change. The information may be provided by the system to reach out and ensure that patients are provided with information regarding the side effects: e.g., generating a message that the detected side effects are normal and should not be a reason to stop taking the pills in response to a determination that the detected side effects are within a bearable level or below a predetermined qualitative or quantitative threshold, which may be set beforehand by a client.

The number of doses the patients are taking may be determined based on container readings, or based on patient input, or both. Patient doses are compared to their prescription, and in response to a determination that patients have fewer than a certain number of days left, i.e., e.g., about 5 days left, or in response to a determination that a schedule is paused, or adjusted for doses administered, the system may automatically contact the pharmacy and inform the pharmacy, via messaging or other information transmitted via an API connected with the system and the pharmacy, that a patient is in need of refills. The automatic contact helps the pharmacies by reducing their workload, as the pharmacies no longer have to make uneducated guesses regarding an appropriate time to contact the patients for their refills or for other status. The method 1810 and message classification 1830 are provided to determine potential support team actions 1840.

Figure 19:
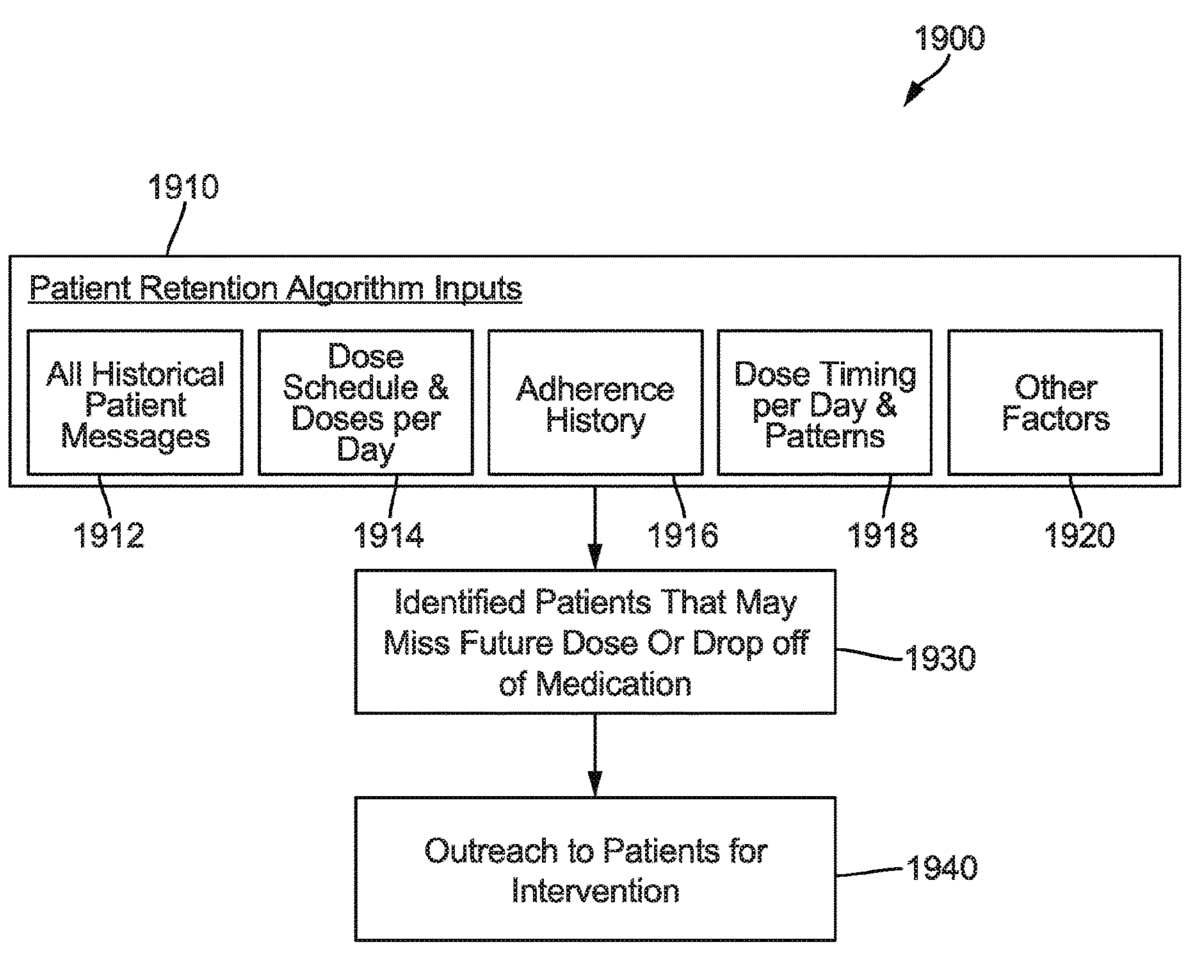
FIG. 19 shows a process flow diagram for identifying patients that may miss a future does or drop off of a medication, and for outreach to patients for an intervention according to an exemplary embodiment of the present disclosure.

FIG. 19 shows a method 1900 for message classification and prioritization to ensure patient adherence. One or more steps of the methods described herein may be executed by a controller. Method 1900 includes patient retention algorithm inputs 1910, including historical patient messages 1912, dose schedule and doses per day 1914, adherence history 1916, dose timing per day and patterns 1918, and other factors 1920. In accordance with the method 1900, an algorithm is executed by the system that tags inbound text messages as either "action required" or "no action required," or the like. The "action required" patients are identified patients that may miss future dose(s) or drop off of a medication 1930. The method 1900 ensures outreach to patients for intervention 1940, for those identified patients. NLP and keyword matching may be employed to determine that a message contains any context for processing by the system to determine whether the patient was responding to a question or informing why the patient missed a dose, which are actions that do not require a response. The system may also access and analyze the patient's history to make sure the patient has acceptable adherence, e.g., storing their historical information in a database, or does not have a substantial amount of previous interactions, and/or whether the patient is a new patient or one that has been in the program for a predetermined length of time. Using the algorithm, a relatively high percentage of messages that need no additional support may be correctly classified. Also, the algorithm is relatively accurate in classifying messages that do need additional support. The method 1900 helps with streamlining any support team's workload, and facilitates communication with patients who need support as rapidly as possible. The method 1900 ensures future patient adherence.

Figure 20:
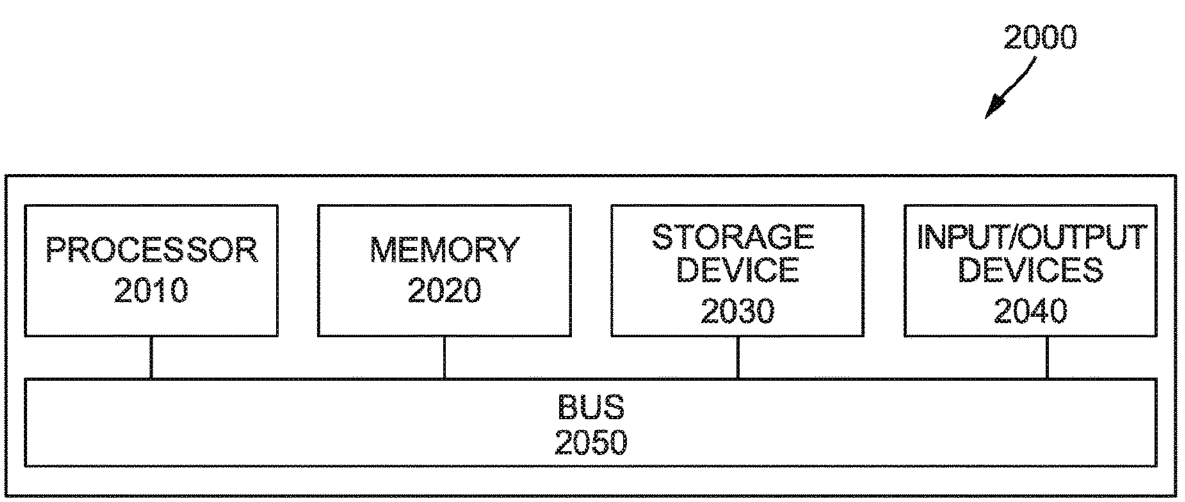
FIG. 20 is a block diagram illustrating a computing system according to an exemplary embodiment of the present disclosure.

As shown in FIG. 20, the computing system 2000 may include a processor 2010, a memory 2020, a storage device 2030, and input/output devices 2040. The processor 2010, the memory 2020, the storage device 2030, and the input/output devices 2040 may be interconnected via a system bus 2050. The processor 2010 is capable of processing instructions for execution within the computing system 2000. The executed instructions may implement one or more components of, for example, the server computer 702, any one of medication containers 100, 200, 300, 400, 500, 600, and/or 800, and/or a system performing operations described in one or more of methods 1300, 1500, 1600, 1700, 1800, and 1900. In some exemplary embodiments of the present disclosure, the processor 2010 may be a single-threaded processor. Alternately, the processor 510 may be a multi-threaded processor. The processor 2010 is capable of processing instructions stored in the memory 2020 and/or on the storage device 2030 to display graphical information for a user interface provided via the input/output device 2040.

The memory 2020 is a computer readable medium, e.g., volatile or non-volatile, that stores information within the computing system 2000. The storage device 2030 is capable of providing persistent storage for the computing system 2000. The storage device 2030 may be a floppy disk device, a hard disk device, an optical disk device, or a tape device, or other suitable persistent storage device. The input/output device 2040 provides input/output operations for the computing system 2000. In some exemplary embodiments of the present disclosure, the input/output device 2040 includes a keyboard and/or pointing device. In various exemplary embodiments, the input/output device 2040 includes a display unit for displaying graphical user interfaces.

According to some exemplary embodiments of the present disclosure, the input/output device 2040 may provide input/output operations for a network device. For example, the input/output device 2040 may include Ethernet ports or other networking ports to communicate with one or more wired and/or wireless networks (e.g., a local area network (LAN), a wide area network (WAN), the Internet).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in the present specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Although at least one exemplary embodiment is described as using a plurality of units to perform the exemplary process, it is understood that the exemplary processes may also be performed by one or plurality of modules. Additionally, it is understood that the term controller/control unit may refer to a hardware device that includes a memory and a processor. The memory may be configured to store the modules and the processor may be specifically configured to execute said modules to perform one or more processes which are described further below.

The use of the terms "first", "second", "third" and so on, herein, are provided to identify the operations, without describing the order of the operations, and the operations may be executed in a different order from the stated order unless a specific order is definitely specified in the context.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium may also be distributed in network coupled computer systems so that the computer readable media is stored and executed in a distributed fashion, e.g., by a telematics server or a Controller Area Network (CAN).

Unless specifically stated or obvious from context, as used herein, the term "about" is understood as within a range of normal tolerance in the art, for example within 2 standard deviations of the mean. "About" may be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

A medication container may be provided that may include one or more sensors, including a capacitance sensor, for sensing information including the contents of the medication container (e.g., pill count or quantity of liquid medication), and transmitting the sensed information to a processor as electronic data. A capacitor is a nonlinear electronic component that is capable of storing an electric charge. Traditionally, a capacitor contains two conductive plates separated by a material with determined dielectric properties. The material is chosen based on an ability of the material to store energy and determines the overall capacitance. A change in the material, including material type or thickness, results in a change of capacitance. The present disclosure includes interdigital capacitors (IDC) to detect medication within a medication container, including a pill bottle. For example, and IDC may correspond to a variable capacitor that changes capacitance based on the material (type and quantity) that is resting above it. A reference IDC may be provided to adjust for humidity and temperature. Changes in capacitance measured by an IDC may correspond to the removal of one or more doses of a medication from a medication container. Reminders and/or alerts to the patient may be triggered based at least in part on the contents (number of doses) of the medication container, a determination that a cap of the container was opened and/or closed, a determination of a time associated with the opening or closing of the cap of the container, the location of the medication container, and/or the container's surroundings. The IDC and the reference IDC may, for example, be located or embedded with the bottom of a medication container to sense a capacitance associated with medication within the medication container and above the IDC and reference IDC sensors.

In one exemplary embodiment, data from one or more medication containers may be provided by a system and method that includes one or more data providers that are in communication with a central processor via a digital communication network. The one or more data providers may include patients, health care providers (HCPs), and/or physical containers for containing and monitoring medication, and which may include sensors, one or more processors and/or one or more transceivers. The central processor may include one or more data processors for executing one or more computer-implemented programs, including artificial intelligence programs, natural language processing programs, and/or data analytics programs.

The one or more algorithms may be configured to manage adherence to a medication program, as administered by an HCP. The one or more algorithms may include, without limitation: an algorithm that reliably estimates that patients will likely drop off of the medication and a time associated with the estimate of the likely drop off of the medication; an algorithm that reliably estimates that patients will need a specific intervention and a time associated with the estimate of the need for the specific intervention; an algorithm that reliably estimates that patients may have a side effect and a time associated with the estimate of the side effect; an algorithm that reliably process patient messages to execute action, which increases adherence; and an algorithm that predicts the impact of schedule changes on future adherence.

Exemplary embodiments of the present disclosure include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which may include a non-transitory computer-readable or machine-readable storage medium, may include, encode, store, or the like one or more programs that cause one or more processors to perform one or more of the operations described herein. Computer implemented methods consistent with one or more exemplary embodiments of the present disclosure may be implemented by one or more data processors residing in a single computing system or multiple computing systems. The multiple computing systems may be connected and may exchange data and/or commands or other instructions or the like via one or more connections, including but not limited to a connection over a network (e.g. the Internet, a wireless wide area network, a local area network, a wide area network, a wired network, or the like), via a direct connection with one or more of the multiple computing systems, etc.

One or more features of the present disclosure described herein may be realized in digital electronic circuitry, integrated circuitry, specially designed application specific integrated circuits (ASICs), field programmable gate arrays (FPGAs) computer hardware, firmware, computer-implemented programs, and/or combinations thereof. The various features may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server are generally remote from each other and may interact through a communication network. The relationship of client and server arises by virtue of computer programs running on the respective computers and having a client-server relationship to each other.

The computer programs, which may also be referred to programs, software, software applications, applications, components, or code, include machine instructions for a programmable processor, and may be implemented in a high-level procedural language, an object-oriented programming language, a functional programming language, a logical programming language, and/or in assembly/machine language. As used herein, the term "machine-readable medium" refers to any computer program product, apparatus and/or device, including for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store the machine instructions non-transitorily, including for example in a manner similar to a non-transient solid-state memory or a magnetic hard drive or any equivalent storage medium. The machine-readable medium may alternatively or additionally store the machine instructions in a transient manner, including for example in a manner similar to a processor cache or other random access memory associated with one or more physical processor cores.

To provide for interaction with a user, one or more features of the present disclosure described herein may be implemented on a computer having a display device, including for example a cathode ray tube (CRT) or a liquid crystal display (LCD) or a light emitting diode (LED) monitor for displaying information to the user and a keyboard and a pointing device, including for example a mouse or a trackball, by which the user may provide input to the computer. Other types of devices may be provided for interaction with a user as well. For example, feedback provided to the user may be any form of sensory feedback, including for example visual feedback, auditory feedback, or tactile feedback; and input from the user may be received in any form, including, but not limited to, acoustic, speech, or tactile input. Other possible input devices include, but are not limited to, touch screens or other touch-sensitive devices including single or multi-point resistive or capacitive trackpads, voice recognition hardware and computer-implemented programs, optical scanners, optical pointers, digital image capture devices and associated interpretation software, and the like.

Related apparatuses, systems, techniques and articles are also described. Computer program products are described that comprise non-transitory computer readable media storing instructions, which when executed by at least one programmable processors of one or more computing systems, causes at least one programmable processor to perform operations herein. Similarly, computer systems are also described that may include one or more programmable processors and a memory coupled to the one or more programmable processors. The memory may temporarily or permanently store instructions that cause at least one programmable processor to perform one or more of the operations described herein. In addition, methods may be implemented by one or more programmable processors either within a single computing system or distributed among two or more computing systems.

The terminology used herein is for the purpose of describing particular exemplary embodiments and is not intended to be limiting. As used herein, "and/or" includes any and all combinations of one or more described items. Use of terms including "comprises" and/or "comprising" specifies the inclusion and presence of stated features, attributes, and components but does not preclude the inclusion or addition of one or more other features, attributes, and components.

As used herein, phrases including "at least one of" or "one or more of" may occur followed by a conjunctive list of elements or features. The term "and/or" may also occur in a list of two or more elements or features. Unless otherwise implicitly or explicitly contradicted by the context in which it is used, a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." In addition, any use of the term "based on" above is intended to mean, "based at least in part on," and an unrecited feature or element is also permissible. Further, as used herein, the singular terms "a," "an," and "the" may include the plural reference unless the context clearly indicates otherwise.

Unless otherwise defined, all terms used herein have the same meaning as commonly understood by one having ordinary skill in the art of medication containers, a medication regimen, and related systems and computer-implemented methods. The meaning of terms used in the present description should be interpreted as having meaning consistent with their meaning in the context of the relevant art.

The present disclosure is to be considered as an exemplification of the claimed exemplary embodiment(s) and is not intended to limit those exemplary embodiments to the specific exemplary embodiments illustrated by the figures.

We claim:

1. An apparatus for medication management, comprising:
- a housing for a packet of medication, wherein the packet of medication includes a plurality of projections positioned on a backing and arranged in a grid format of multiple rows and columns, each of the plurality of projections houses a respective portion of the medication;
- a sensor coupled to the housing for sensing whether the packet of medication has been removed or is likely to have been removed from the housing, the sensing being based on a state of a top of the housing relative to a base of the housing during a particular duration; and
- a transmitter for wirelessly transmitting, to a remote computer, data regarding a reading of the sensor, the data representative of whether the packet of medication has been removed or likely to have been removed from the housing.

2. The apparatus of claim 1, wherein:
- the housing includes a first housing and a second housing;
- the sensor includes a first sensor coupled to the first housing;
- the sensor includes a second sensor coupled to the second housing;
- the first sensor is proximate to the second sensor in a first state of the first housing and the second housing disposed in a closed position; and
- the first sensor is positioned a spaced distance apart from the second sensor in a second state of the first housing and the second housing disposed in an open position.

3. The apparatus of claim 2, wherein:
- the first housing is a base;
- the second housing is a top;
- the top is coupled via a hinge to the base along a long edge of each of the base and the top; and
- the first sensor and the second sensor are provided opposite the hinge.

4. The apparatus of claim 2, wherein:
- the first housing is a base;
- the second housing is a cap;
- the cap is coupled via a hinge to the base along a short edge of each of the base and the cap; and
- the first sensor and the second sensor are provided proximate to the short edge.

5. The apparatus of claim 2, wherein:
- the first housing is a base;
- the second housing is a top;
- the top is coupled via a hinge to the base along a short edge of each of the base and the top; and
- the first sensor and the second sensor are provided opposite the short edge.

6. The apparatus of claim 2, wherein:
- the first housing is a base having an open end;
- the second housing is a tray configured to slide into and out of the base via the open end of the base; and
- the first sensor and the second sensor are provided proximate to a short edge in the first state of the base and the tray disposed in a closed position.

7. The apparatus of claim 1, wherein:
- the housing includes a base having an open end;
- the sensor includes a first sensor coupled to a first interior surface of the base;
- the sensor includes a second sensor coupled to a second interior surface of the base opposite the first interior surface; and
- the first sensor and the second sensor are positioned at or proximate to the open end.

8. The apparatus of claim 1, wherein:
- the housing includes a base having a surface configured to be coupled to and decoupled from the packet of medication;
- the sensor includes a first sensor coupled to the base;
- the sensor includes a second sensor coupled to the packet of medication;
- the first sensor is proximate to the second sensor in a first state of the base coupled to the packet of medication; and
- the first sensor is positioned a spaced distance apart from the second sensor in a second state of the base decoupled from the packet of medication.

9. The apparatus of claim 1, wherein the sensor comprises at least one of a magnet switch, a reed switch, a magnet sensor, a hall effect sensor, an optical sensor, a pressure sensor, a capacitance sensor, a capacitive touch sensor, an inductive touch sensor, a proximity sensor, or an electrical contact.

10. A system for medication management, the system configured to communicate with an apparatus for medication management, the apparatus comprising:
- a housing for a packet of medication, wherein the housing includes a base and a top;

a sensor coupled to the housing for sensing whether the packet of medication has been removed or is likely to have been removed from the housing, wherein:

the sensing being based on a state of a top of the housing relative to a base of the housing during a particular duration, and the packet of medication includes a plurality of projections arranged in a grid format of multiple rows and columns; and a transmitter for wirelessly transmitting data regarding a reading of the sensor to a remote computer, the data representative of whether the packet of medication has been removed or likely to have been removed from the housing.

11. A system comprising:

a housing for medication, the housing having an open end and a closed end opposite the open end;

a sensor coupled to the housing for sensing a quantity of medication within the housing;

wherein:

the sensor comprises a plurality of conductive electrodes arranged in an interleaved pattern for sensing the quantity of medication within the housing;

the sensor is provided proximate to the closed end; and the sensor is provided in the housing in a substantially horizontal position in a state of the housing in an upright position.

12. The system of claim 11, wherein the plurality of conductive electrodes arranged in the interleaved pattern comprise regularly-spaced conductive electrodes.

13. The system of claim 11, wherein the plurality of conductive electrodes arranged in the interleaved comprise rectangularly shaped or generally rectangularly shaped conductive electrodes.

14. The system of claim 11, wherein:

a gap is disposed between at least two of the plurality of conductive electrodes arranged in the interleaved pattern; and a length of the gap is about 1 mm.

15. The system of claim 11, comprising:

one or more processors configured to trigger a reading of the sensor;

a transmitter for wirelessly transmitting data regarding the reading of the sensor to a remote computer; and a wireless receiver configured to receive an activation command from or otherwise initiated by the remote computer;

wherein the one or more processors is configured to activate an alert based at least in part on the receipt of the activation command by the wireless receiver.

16. The system of claim 15, wherein at least one of the one or more processors includes one from a variable oscillating circuit, a resonant circuit, a Wein bridge oscillator, or a switched capacitor circuit.

* * * * *